(12) United States Patent
Koch

(10) Patent No.: US 12,026,890 B2
(45) Date of Patent: Jul. 2, 2024

(54) LUMINESCENCE IMAGING WITH REFINING LOOP BASED ON COMBINATION OF PARTIAL ILLUMINATIONS

(71) Applicant: SurgVision GmbH, Munich (DE)

(72) Inventor: Maximilian Koch, Amsterdam (NL)

(73) Assignee: SurgVision GmbH, Munich (DE)

( * ) Notice: Subject to any disclaimer, the term of this patent is extended or adjusted under 35 U.S.C. 154(b) by 275 days.

(21) Appl. No.: 17/620,079

(22) PCT Filed: Jun. 16, 2020

(86) PCT No.: PCT/EP2020/066558
§ 371 (c)(1),
(2) Date: Dec. 16, 2021

(87) PCT Pub. No.: WO2020/254287
PCT Pub. Date: Dec. 24, 2020

(65) Prior Publication Data
US 2022/0309678 A1   Sep. 29, 2022

(30) Foreign Application Priority Data
Jun. 18, 2019   (EP) ..................................... 19180867

(51) Int. Cl.
*G06T 7/174*   (2017.01)
*A61B 5/00*   (2006.01)
(Continued)

(52) U.S. Cl.
CPC ............ *G06T 7/174* (2017.01); *A61B 5/0071* (2013.01); *G06T 7/0016* (2013.01); *G06T 7/11* (2017.01);
(Continued)

(58) Field of Classification Search
CPC ......... G06T 7/174; G06T 7/0016; G06T 7/11; G06T 2207/10064; G06T 2207/10152;
(Continued)

(56) References Cited

U.S. PATENT DOCUMENTS 8,532,398 B2 * 9/2013 Filkins .................. G02B 21/16
382/128
9,134,236 B2 * 9/2015 Bednarkiewicz .... G02B 21/365
(Continued)

OTHER PUBLICATIONS

Bednarkiewicz, et al., "Global Analysis of Microscopic Fluorescence Lifetime Images Using Spectral Segmentation and a Digital Micromirror Spatial Illuminator", Journal of Biomedical Optics, Jul./Aug. 2008, vol. 13(4), pp. 041316-1 through 041316-13.
(Continued)

*Primary Examiner* — Michael S Osinski
(74) *Attorney, Agent, or Firm* — FisherBroyles LLP; Bryan A. Santarelli

(57) ABSTRACT

A solution is proposed for imaging an object containing a luminescence substance. A corresponding method (500) is based on a refining loop. At each iteration of the refining loop, different spatial patterns are determined (516-518, 524;536-540, 546), partial illuminations corresponding to the spatial patterns are applied to the object (520,526;542, 548), component images are acquired in response to the partial illuminations (522,528;544,550) and the component images are combined (530;552) into a combined image. A corresponding system (100) is also proposed. Moreover, a computer program (400) and a corresponding computer program product are proposed. A diagnostic method, a surgical method and a therapeutic method based on the same solution are further proposed.

28 Claims, 14 Drawing Sheets

(51) Int. Cl.
*G06T 7/00* (2017.01)
*G06T 7/11* (2017.01)
*G06V 10/22* (2022.01)
*G06V 10/60* (2022.01)

(52) U.S. Cl.
CPC .............. *G06V 10/22* (2022.01); *G06V 10/60* (2022.01); *G06T 2207/10064* (2013.01); *G06T 2207/10152* (2013.01); *G06T 2207/20212* (2013.01); *G06T 2207/30088* (2013.01); *G06V 2201/03* (2022.01)

(58) Field of Classification Search
CPC . G06T 2207/20212; G06T 2207/30088; G06T 7/0012; G06T 2207/10056; G06T 2207/10068; G06T 2207/30004; A61B 5/0071; A61B 1/043; A61B 1/0638; A61B 1/00006; A61B 1/000094; A61B 5/0059; A61B 1/00; A61B 1/00009; A61B 1/0005; G06V 10/22; G06V 10/60; G06V 2201/03; G01N 21/6458; G02B 21/16; G02B 21/367; G02B 21/0012; G02B 23/24; G02B 21/361
See application file for complete search history.

(56) References Cited

U.S. PATENT DOCUMENTS

| | | | |
|---|---|---|---|
| 10,607,316 B2 * | 3/2020 | Kato | G06T 5/70 |
| 10,839,509 B2 * | 11/2020 | Goodman | G06T 7/0012 |
| 11,156,821 B2 * | 10/2021 | Chen | G02B 21/086 |
| 11,229,353 B2 * | 1/2022 | Ganapati | A61B 5/7425 |
| 11,555,992 B2 * | 1/2023 | Chen | G02B 21/361 |
| 11,599,738 B2 * | 3/2023 | Schie | G06T 7/136 |
| 11,719,920 B2 * | 8/2023 | Kamada | G02B 21/0028 359/368 |
| 11,771,324 B1 * | 10/2023 | Strasfeld | G01N 33/4833 600/431 |
| 11,867,896 B2 * | 1/2024 | Usuda | A61B 1/00045 |
| 2009/0202119 A1 * | 8/2009 | Hefti | A61B 5/0059 382/128 |
| 2011/0226965 A1 * | 9/2011 | Wolleschensky | G02B 27/58 250/459.1 |
| 2011/0235875 A1 | 9/2011 | Filkins et al. | |
| 2013/0010098 A1 * | 1/2013 | Kalkbrenner | G01N 21/6458 348/79 |
| 2017/0307440 A1 * | 10/2017 | Urban | G01N 21/6458 |
| 2018/0338679 A1 * | 11/2018 | Schallek | A61B 3/145 |
| 2019/0287774 A1 * | 9/2019 | Ogata | H01J 49/0004 |
| 2019/0379840 A1 * | 12/2019 | Frangioni | A61B 1/0005 |
| 2020/0204776 A1 * | 6/2020 | Themelis | A61B 90/30 |
| 2020/0320673 A1 * | 10/2020 | Benson | G06T 7/174 |
| 2020/0397268 A1 * | 12/2020 | Ganapati | A61B 5/0077 |
| 2021/0106215 A1 * | 4/2021 | Shinji | A61B 1/0638 |
| 2021/0153720 A1 * | 5/2021 | Usuda | A61B 1/07 |
| 2021/0209818 A1 * | 7/2021 | Travish | A61B 6/4007 |
| 2022/0284570 A1 * | 9/2022 | Tan | G06T 7/62 |

OTHER PUBLICATIONS

Xin, et al., "Digital Micro-Mirror Device Based Modulator for Microscope Illumination", Physics Procedia, Jun. 14, 2009, pp. 87 through 91, Published: CN.

International Searching Authority, "International Search Report and Written Opinion from PCT Application No. PCT/EP2020/066558 dated Sep. 18, 2020", from Foreign Counterpart, pp. 1-13, Published in: WO.

* cited by examiner

LUMINESCENCE IMAGING WITH REFINING LOOP BASED ON COMBINATION OF PARTIAL ILLUMINATIONS

This application claims priority to International Patent Application No. PCT/EP2020/066558 filed on Jun. 16, 2020.

TECHNICAL FIELD

The present disclosure relates to imaging applications. More specifically, this disclosure relates to luminescence imaging.

BACKGROUND ART

The background of the present disclosure is hereinafter introduced with the discussion of techniques relating to its context. However, even when this discussion refers to documents, acts, artifacts and the like, it does not suggest or represent that the discussed techniques are part of the prior art or are common general knowledge in the field relevant to the present disclosure.

Imaging generally relates to a number of techniques that allow acquiring images of objects (typically, not visible directly) in a substantially non-invasive manner. For example, imaging techniques are routinely exploited in equipment for medical applications to inspect (inner) body-parts of patients or samples thereof for diagnostic, therapeutic and/or surgical purposes.

A specific imaging technique increasingly considered is luminescence imaging, and especially fluorescence imaging. Luminescence imaging is based on a luminescence phenomenon, consisting of the emission of light by (luminescence) substances when subject to any excitation different from heating; particularly, a fluorescence phenomenon occurs in certain substances, called fluorophores, which emit light when they are illuminated. More in detail, the fluorophores pass to an excited (electronic) state when they absorb excitation light at a wavelength within an excitation spectrum of the fluorophores. The excited state is unstable, so that the fluorophores very shortly decay therefrom to a ground (electronic) state. As the fluorophores decay, they emit (fluorescence) light at a characteristic wavelength (longer than the one of the excitation light because of energy dissipated as heat in the excited state). An intensity of the fluorescence light depends on an amount of the fluorophores that are illuminated.

Fluorescence imaging in medical applications is generally based on administration of fluorescence agents. Particularly, Fluorescence Molecular Imaging (FMI) applications are based on the use of targeted fluorescence agents. Each targeted fluorescence agent is adapted to reaching a specific molecule of a desired target and then to remain immobilized thereon (for example, thanks to a specific interaction with tumoral tissues). The fluorescence light that is emitted by the immobilized (targeted) fluorescence agent allows detecting the corresponding target (tumoral tissues in the example at issue). Particularly, structured illumination may be exploited. In this case, the excitation light is modulated spatially with a periodic pattern. Since tissues act as a spatial low-pass filter, in this way it is possible to separate superficial features from deep features.

Fluorescence imaging may be used for a number of purposes in medical applications. For example, a representation of the (immobilized) fluorescence agent in the images of the body-parts allows identifying corresponding lesions (which would otherwise be difficult to identify); moreover, the intensity of the fluorescence light that is emitted by the fluorescence agent allows quantifying the lesions. This information may be used in diagnostic applications for discovering or monitoring lesions, in therapeutic applications for delineating lesions to be treated and in surgical applications for recognizing margins of lesions to be resected.

Fluorescence imaging is very practical, since the fluorescence agents have low cost, may be prepared in large batches thanks to their high stability, are easy to handle and simple to dispose of, and allow concurrent detection of different targets by using corresponding targeted contrast agents based on fluorophores emitting fluorescence lights at different wavelengths.

Nevertheless, the performance of fluorescence imaging is limited by optical properties of the tissues, i.e., scattering and absorption. Particularly, excitation lights at visible wavelengths only allow imaging body-parts at very low (penetration) depth inside them (no more than 100 μm). Therefore, excitation lights at higher wavelengths (reducing the absorption by the tissues acting as optical long-pass filter) are commonly used to improve the penetration depth; for example, excitation lights at Near InfraRed (NIR) wavelengths, i.e., 750-900 nm, allow imaging body-parts up to 1-2 cm inside them.

However, NIR lights increase the scattering by the tissues. This degrades the quality of the obtained images of the body-part. Particularly, the images become relatively diffused; moreover, targets at different depths in the body-parts may become intermingled. All of the above hinders the detection of the desired targets in the body-parts. For example, in diagnostic applications this adversely affects the identification and/or the quantification of the corresponding lesions, which may lead to misinterpretations (with the risk of false positives/negatives and wrong follow-up). In therapeutic applications, this adversely affects the delineation of the corresponding lesions to be treated (with the risk of reduced effectiveness of a therapy or of damages to healthy tissues). In surgical applications, this leads to uncertainty about the precise recognition of the margins of the lesions (with the risk of incomplete resection of the lesions or excessive removal of healthy tissues).

SUMMARY

A simplified summary of the present disclosure is herein presented in order to provide a basic understanding thereof, however, the sole purpose of this summary is to introduce some concepts of the disclosure in a simplified form as a prelude to its following more detailed description, and it is not to be interpreted as an identification of its key elements nor as a delineation of its scope.

In general terms, the present disclosure is based on the idea of applying a refining loop based on partial illuminations.

Particularly, an aspect provides a method for imaging an object containing a luminescence substance. The method is based on a refining loop. At each iteration of the refining loop, different spatial patterns are determined, partial illuminations corresponding to the spatial patterns are applied to the object, component images are acquired in response to the partial illuminations and the component images are combined into a combined image.

A further aspect provides a computer program for implementing the method.

A further aspect provides a corresponding computer program product.

A further aspect provides a system for implementing the method.

A further aspect provides a corresponding diagnostic method.

A further aspect provides a corresponding therapeutic method.

A further aspect provides a corresponding surgical method.

More specifically, one or more aspects of the present disclosure are set out in the independent claims and advantageous features thereof are set out in the dependent claims, with the wording of all the claims that is herein incorporated verbatim by reference (with any advantageous feature provided with reference to any specific aspect that applies mutatis mutandis to every other aspect).

BRIEF DESCRIPTION OF THE DRAWINGS

The solution of the present disclosure, as well as further features and the advantages thereof, will be best understood with reference to the following detailed description thereof, given purely by way of a non-restrictive indication, to be read in conjunction with the accompanying drawings (wherein, for the sake of simplicity, corresponding elements are denoted with equal or similar references and their explanation is not repeated, and the name of each entity is generally used to denote both its type and its attributes, such as value, content and representation). Particularly.

DETAILED DESCRIPTION

Figure 1:
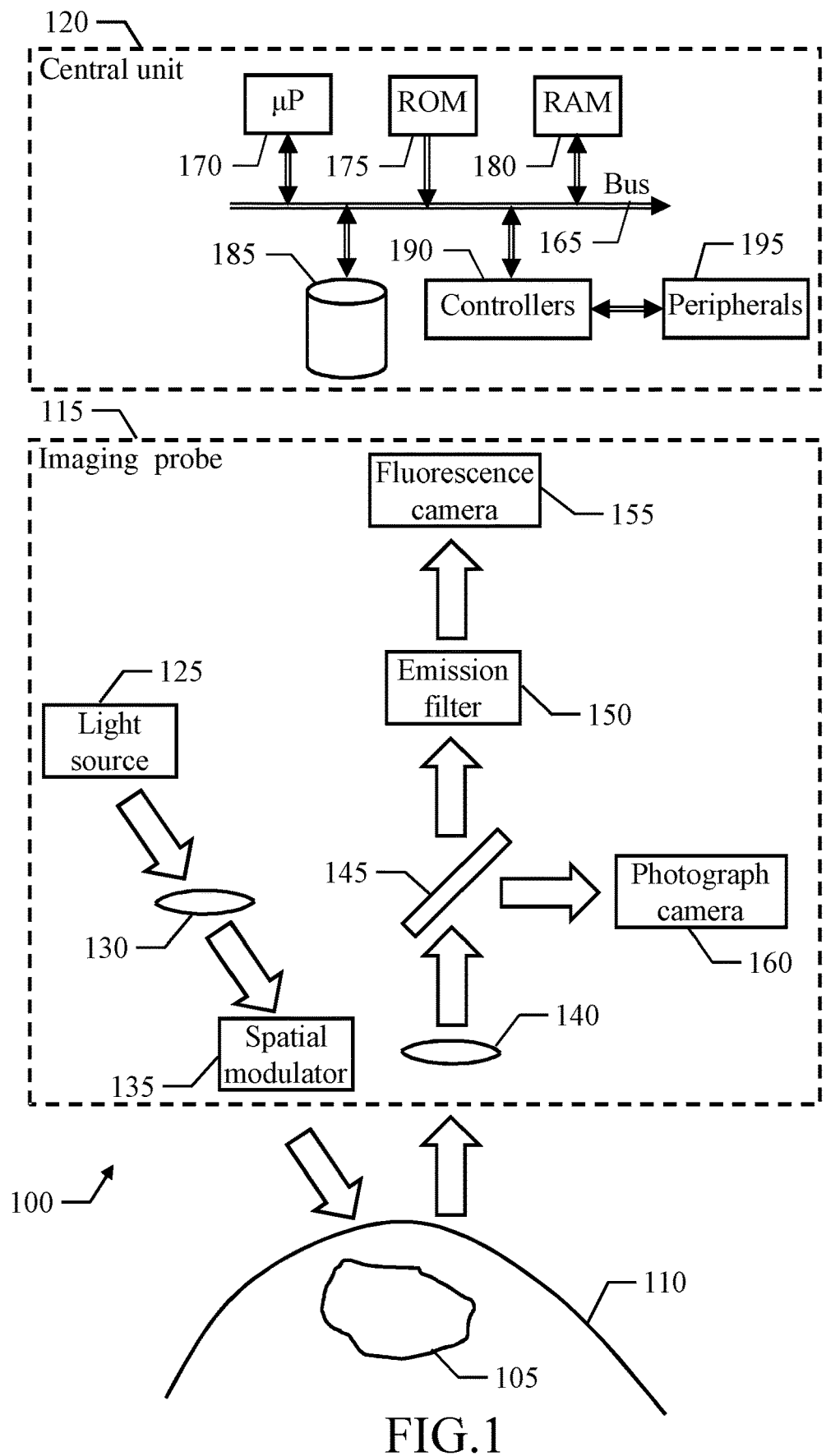
FIG. 1 shows a schematic block diagram of a fluorescence imaging system that may be used to practice the solution according to an embodiment of the present disclosure.

With reference to FIG. 1, a schematic block diagram is shown of a fluorescence imaging system 100 that may be used to practice the solution according to an embodiment of the present disclosure. The (fluorescence) imaging system 100 is used to inspect a body-part 105 of a patient 110 (to which a fluorescence agent has been administered), for example, for diagnostic, therapeutic and/or surgical purposes.

The imaging system 100 has an imaging probe 115 for acquiring an image of the body-part 105 and a central unit 120 for controlling its operation.

Starting from the imaging probe 115, it comprises the following components.

A light source 125 generates an excitation light for illuminating the body-part 105, with wavelength and energy suitable to excite the fluorophores of the fluorescence agent (for example, of NIR type) previously administered to the body-part 105, for example, intravenously or locally. The light source 125 may be a laser (generating a narrow beam of collimated, coherent light at a specific wavelength) provided with a filter (selecting a desired wavelength if the laser produces multiple wavelengths of light and cleaning up the excitation light from unwanted spurious wavelengths in any case). In another implementation, the light source may be based on a solid-state Light Emitting Diode (LED), or a combination or stack of multiple LEDs of sufficient spectral properties and optical power (again with a clean-up filter). In yet another implementation, the light source may be based on black-body radiation of a filament-based light-bulb or gas-discharge based luminant (such as a halogen or a Xenon-discharge lamp), equipped with sufficient optical devices to restrict to desired wavelengths (for example, spectral band-pass filters, cold-mirror-reflectors or a combination thereof). Delivery optics 130 deliver the excitation light generated by the light source 125. For example, the delivery optics 130 comprise a rigid light-guide, such as based on lenses and mirrors (guiding the excitation light along a corresponding optical path), or a flexible light-guide, such as a single light-guiding fiber, a fiber-bundle, or a liquid light guide. A spatial modulator 135 receives the excitation light via the delivery optics 130, modulates it spatially (as described in detail in the following) and then applies a corresponding illumination to the body-part 105. In the example at issue, wherein the excitation light provided by the laser of the light source 125 is a beam illuminating a point only, for this purpose the spatial modulator 135 rapidly moves the beam in two dimensions (by a system of galvanometric mirrors) to scan a whole surface of the body-part 105. For example, the spatial modulator 135 may be a Digital Mirror Device, or DMD (providing selective reflection controlled by micro-mechanical structures), a Liquid Crystal Display, or LCD (providing selective trans-illumination controlled electronically), a galvanometric mirror (deflecting an illumination beam depending on electrical currents), and so on. Collection optics 140 collect light from the body-part 105 (in an epi-illumination geometry), comprising the fluorescence light emitted by the fluorescence agent present therein. For example, the collection optics 140 comprise objective lens (focusing the collected light) and confocal optics (blocking out-of-focus collected light not coming from the illuminated point of the body-part 105). A beam-splitter 145 splits the collected light into two channels. For example, the beam-splitter 145 is a dichroic mirror (transmitting and reflecting the collected light at wavelengths above and below, respectively, a characteristic wavelength thereof). In one of the channels of the beam-splitter 145 with the (portion of the) collected light comprising the wavelength of the fluorescence light (such as the transmitted one), an emission filter 150 filters the collected light to remove the wavelengths of the excitation light (which might be reflected by the body-part 105) and of any ambient lights (which might be reflected or generated by background/inherent fluorescence), so as to leave the wavelength of the fluorescence light only. A fluorescence camera 155 receives the (filtered) collected light from the emission filter 150 and generates a corresponding (fluorescence) image representing the fluorescence light that is emitted by the body-part 105. For example, the fluorescence camera 155 is based on a CCD sensor. The CCD sensor comprises an array of CCD cells each accumulating an electric charge proportional to the intensity of the fluorescence light of a corresponding location of the body-part 105 (consisting of a basic portion thereof). A control circuit transfers the electric charge accumulated in each CCD cell to a charge amplifier, which converts it into a corresponding analog voltage. An Analog-to-Digital Converter (ADC) converts each analog voltage into a digital value (which may be left as is to maintain proportionality to the amount of fluorescence agent that is present in the location or may be compressed non-linearly, such as logarithmically, to distribute a digitalization error uniformly). In the other one of the channels of the beam-splitter 145 with the (portion of the) collected light not comprising the wavelength of the fluorescence light (mainly consisting of the reflected light from the body-part 105), a photograph camera 160 (for example, based on a CCD sensor as well) receives the collected light and generates a corresponding (photograph) image representing a visualization the body-part 105. Depending on the desired wavelengths or other design goals, one or more of the cameras might also be implemented by other sensor technologies, such as based on Intensified Charged-Coupled Devices (ICCD), Electron Multiplying Charge-Coupled Device (EMCCD), Complementary Metal-Oxide-Semiconductor (CMOS), Indium Gallium Arsenide (InGaAs), and so on.

Moving to the central unit 120, it comprises several units that are connected among them through a bus structure 165. Particularly, one or more microprocessors (μP) 170 provide processing and orchestration functionalities of the central unit 120. A non-volatile memory (ROM) 175 stores basic code for a bootstrap of the central unit 120 and a volatile memory (RAM) 180 is used as a working memory by the microprocessors 170. The central unit 120 is provided with a mass-memory 185 for storing programs and data (for example, a Solid-State-Disk (SSD)). Moreover, the central unit 120 comprises a number of controllers 190 for peripherals, or Input/Output (I/O) units; particularly, the controllers 190 control the light source 125, the spatial modulator 135, the fluorescence camera 155 and the photograph camera 160 of the imaging probe 115; moreover, the controllers 190 control further peripherals, denoted as a whole with the reference 195, such as a monitor for displaying the image of the body-part 105, a keyboard for entering commands, a trackball for moving a pointer on the monitor, a drive for reading/writing removable storage units (such as optical disks like DVDs) and a network interface card (NIC) for connecting to a communication network (such as a LAN).

With reference now to FIG. 2A-FIG. 2D, an example is shown of application of the solution according to an embodiment of the present disclosure.

Figure 2A:
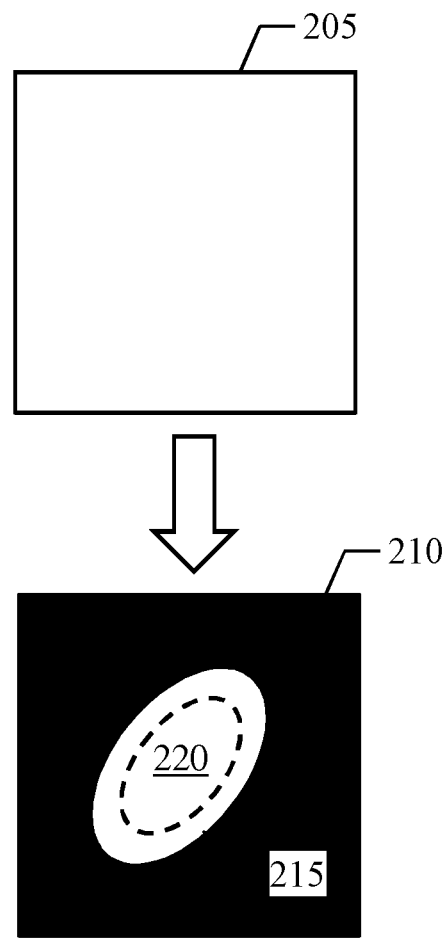
FIG. 2A-FIG. 2D show an example of application of the solution according to an embodiment of the present disclosure.

Starting from FIG. 2A, a starting illumination 205 is applied to the body-part, which comprises a target region containing the fluorescence agent. The starting illumination 205 is based on a starting spatial pattern providing a full illumination (white) of the body-part, so as to make the excitation light reach all the locations thereof. A starting (fluorescence) image 210 is acquired in response to the starting illumination 205. The starting image 210 comprises a detection segment 215 wherein the fluorescence light is detected. Because of the scattering of the tissues in the body-part, the starting image 210 is generally diffused, with the detection segment 215 larger than a target segment 220 actually representing the target region (drawn in dashed lines to denote that it is not discernible in the starting image 210).

Figure 2B:
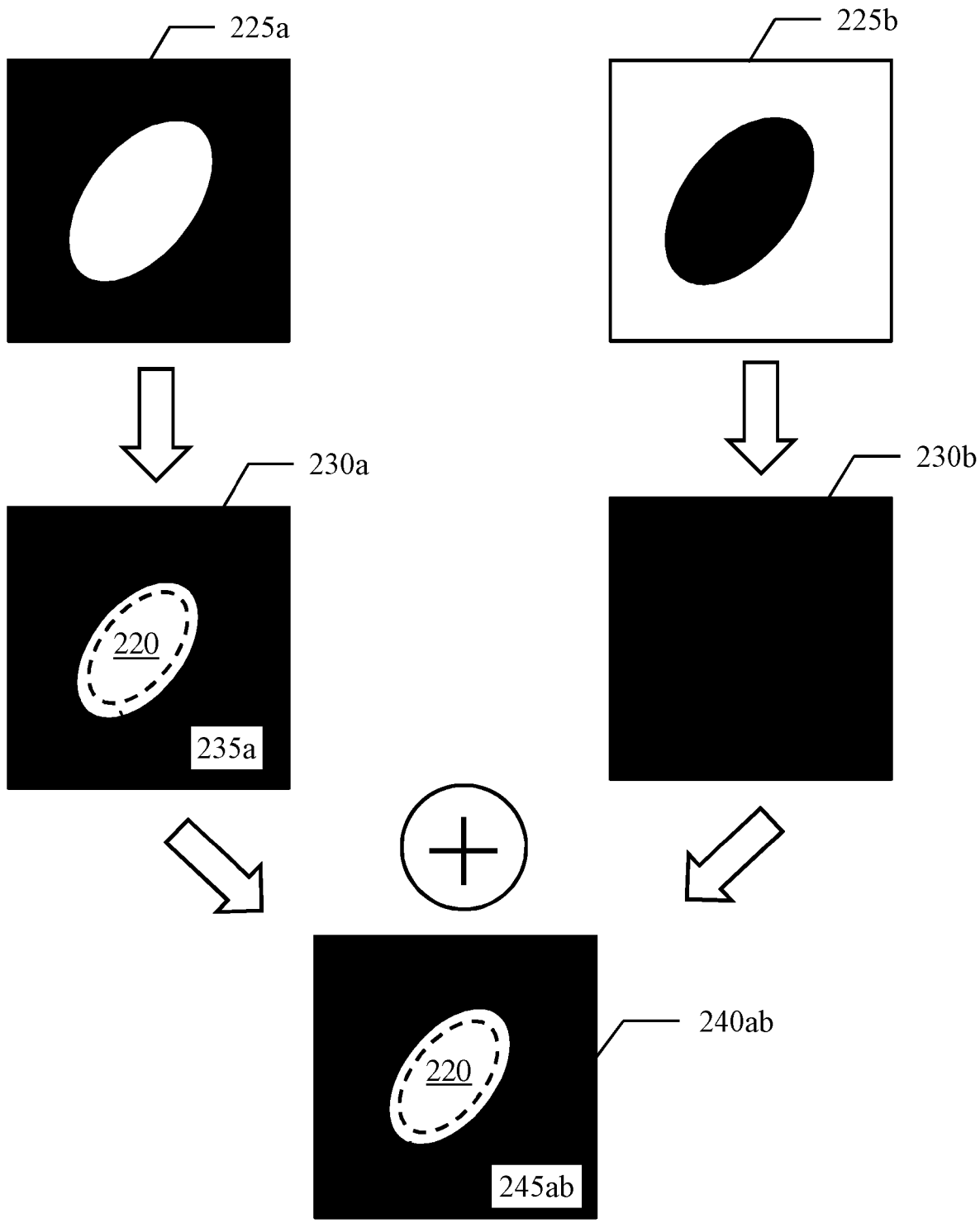

Moving to FIG. 2B, in the solution according to an embodiment of the present disclosure a refining loop is performed for reducing the diffusion. The refining loop works on a combined (fluorescence) image, which is initialized to the starting image. Particularly, a main partial illumination 225a is applied to the body-part. The main partial illumination 225a corresponds to a main spatial pattern providing a full illumination (white) of a region of the body-part corresponding to the detection segment of a previous (version of the) combined image and a non-illumination (black) of a region of the body-part corresponding to a remaining non-detection segment of the previous combined image, to make the excitation light reach and not reach, respectively, the corresponding locations of the body-part. A main component (fluorescence) image 230a is acquired in response to the main partial illumination 225a. The main component image 230a comprises a detection segment 235a wherein the fluorescence light is detected. The missing illumination of the tissues around the target region makes the component image 230a less diffused, with the detection segment 235a smaller than the one in the previous combined image (but still larger than the target segment 220). Moreover, a secondary partial illumination 225b is applied to the body-part. The secondary partial illumination 225b corresponds to a secondary spatial pattern which is the negative of the main spatial pattern of the main partial illumination 225a, providing a non-illumination (black) and an illumination (white) of the regions of the body-part corresponding to the detection segment and to the non-detection segment, respectively, of the previous combined image. A secondary component (fluorescence) image 230b is acquired in response to the secondary partial illumination 225b. Because the target region is not illuminated, in the whole secondary component image 225b no fluorescence light is detected. The (main/secondary) component images 230a and 230b are combined into a (new version of the) combined image 240ab by summing them for each location of the body-part. As a result, the combined image 240ab has a detection segment 245ab (wherein the fluorescence light is detected) the same as the detection segment 235a (larger than the target segment 220).

Figure 2C:
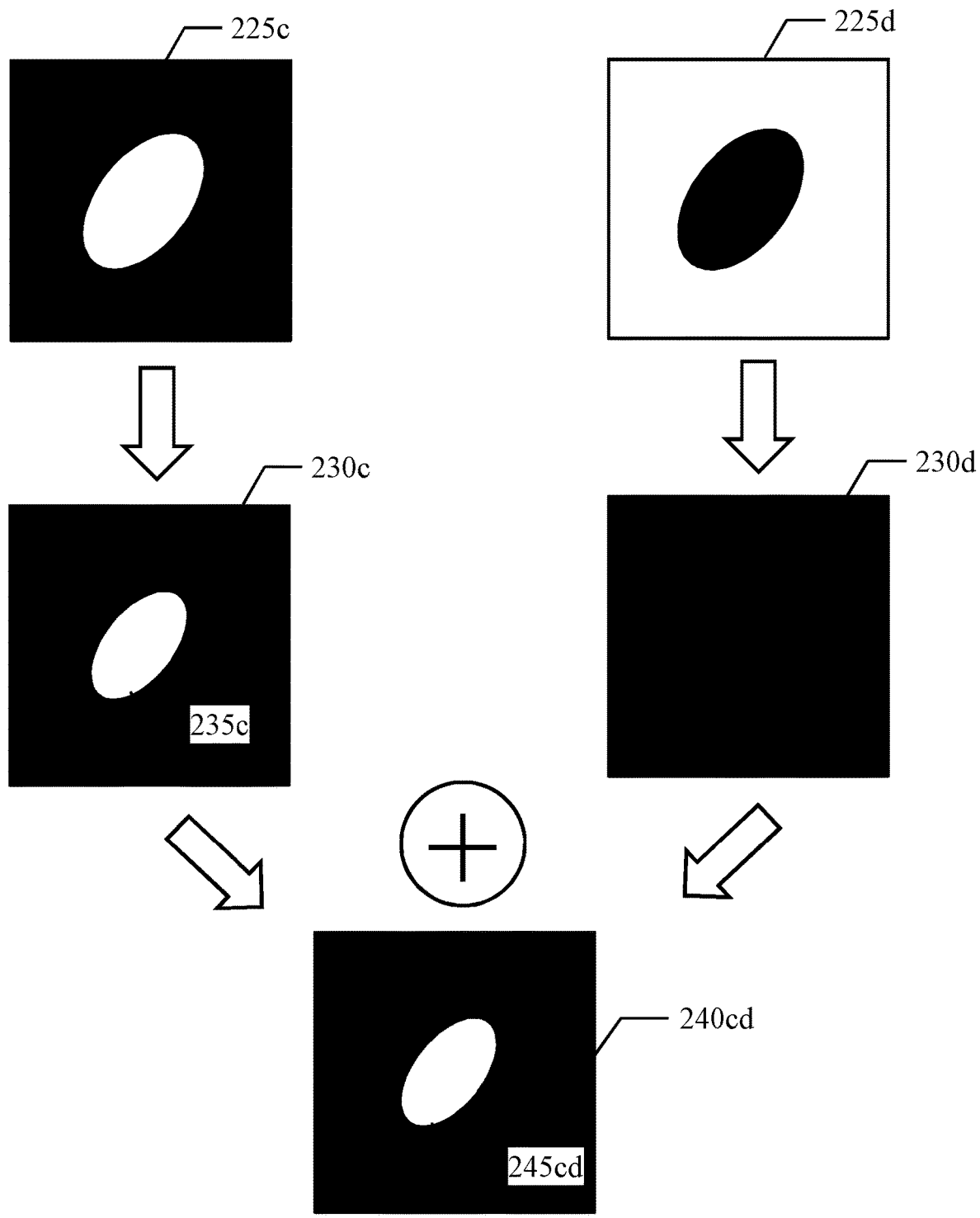

Moving to FIG. 2C, the same operations are repeated at each iteration of the refining loop. Particularly, a main partial illumination 225c, with a main spatial pattern defined according to the previous combined image, is applied to the body-part. A main component (fluorescence) image 230c, comprising a detection segment 235c wherein the fluorescence light is detected, is acquired in response to the main partial illumination 225c. Because the tissues around the target region are lesser and lesser illuminated at each iteration of the refining loop, at a certain point the detection segment 235c becomes substantially the same as the target segment. Moreover, a secondary partial (illumination) 225d, with a secondary spatial pattern being the negative of the main spatial pattern of the main partial illumination 225c, is applied to the body-part. A secondary component (fluorescence) image 230d, again with no fluorescence light being detected, is acquired in response to the secondary partial illumination 225d. The (main/secondary) component images 230c and 230d are combined into a (new version of the) combined image 240cd (by summing them for each location of the body-part). As a result, the combined image 235cd has a detection segment 245cd the same as the detection segment 235c (equal to the target segment).

Figure 2D:
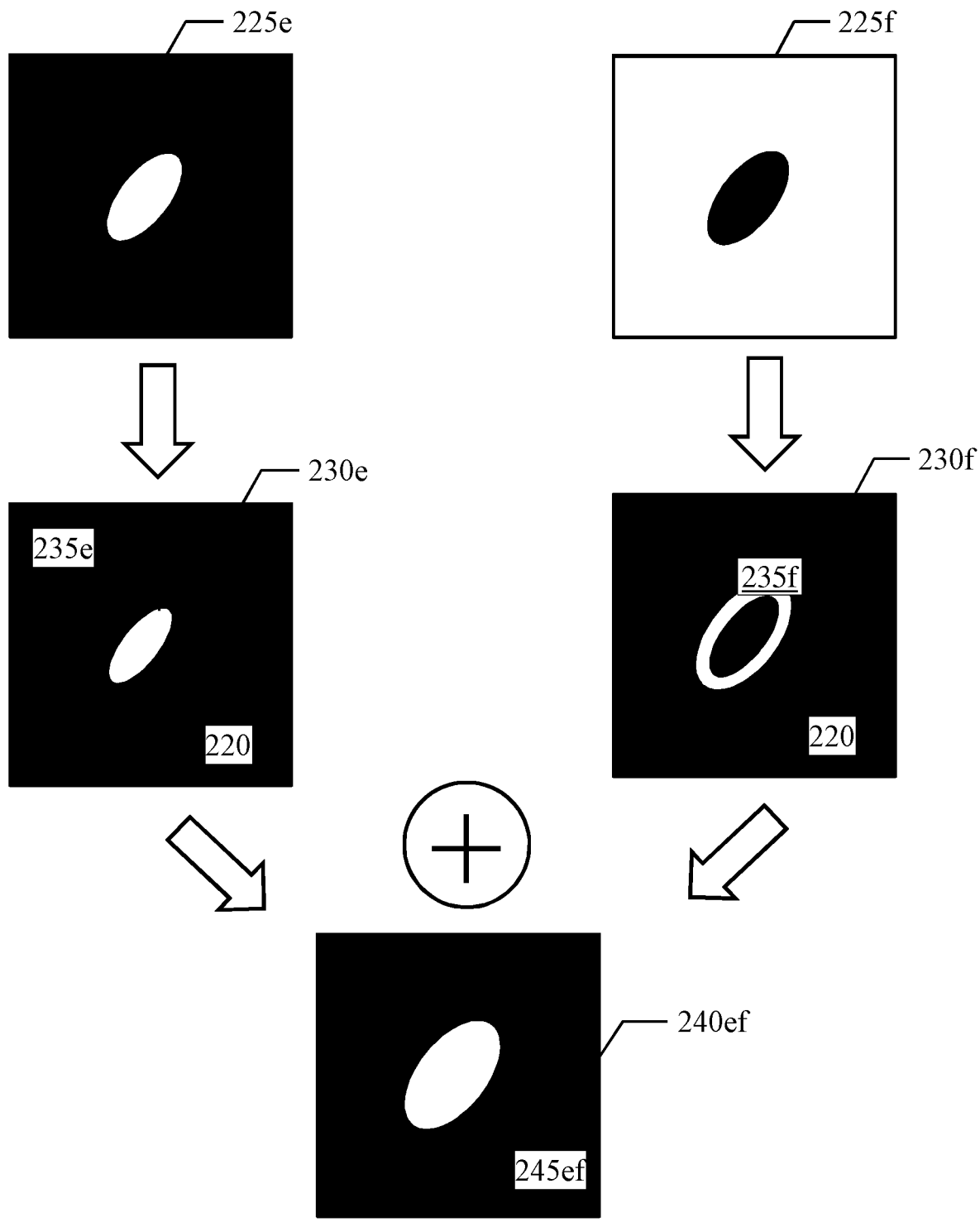

The detection segment of the component image then remains the same as the target segment. Indeed, as shown in FIG. 2D, a main partial illumination 225e might even have a main spatial pattern which provides a main component (fluorescence) image 230e comprising a detection segment 235e smaller than the target segment 220. In this case, however, a secondary partial illumination 225f, with a secondary spatial pattern being the negative of the main spatial pattern of the main partial illumination 225e, would provide a secondary component (fluorescence) image 230f comprising a detection segment 235f for the remaining portion of the target segment 220. Therefore, a (new version of the) combined image 240ed, obtained by summing the (main/secondary) component images 230e and 230f for each location of the body-part, would have a detection segment 245ef given by the union of the detection segment 235e and the detection segment 235f (still equal to the target segment 220).

With reference now to FIG. 3A-FIG. 3E, a further example is shown of application of the solution according to an embodiment of the present disclosure.

Figure 3A:
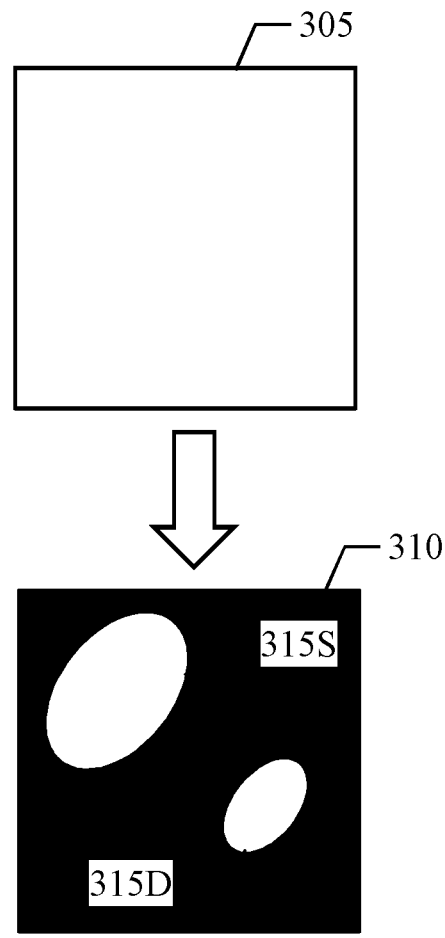
FIG. 3A-FIG. 3E show a further example of application of the solution according to an embodiment of the present disclosure.

Starting from FIG. 3A, a starting illumination 305 is applied to the body-part; as above, the starting illumination 305 is based on a starting spatial pattern providing a full illumination (white) of the body-part. In this case, the body-part comprises two target regions containing the fluorescence agent; particularly, a superficial target region is arranged on a surface of the body-part (for example, skin in diagnostic/therapeutic applications or exposed tissue in surgical applications) and a deep target region is arranged below the surface of the body-part. A starting (fluorescence) image 310 is acquired in response to the starting illumination 305. The starting image 310 comprises two detection segments 315S,315D wherein the fluorescence light is detected; the detection segment 315S represents the superficial target region and the detection segment 315D represents the deep target region (disregarding their diffusion for the sake of simplicity).

Figure 3B:
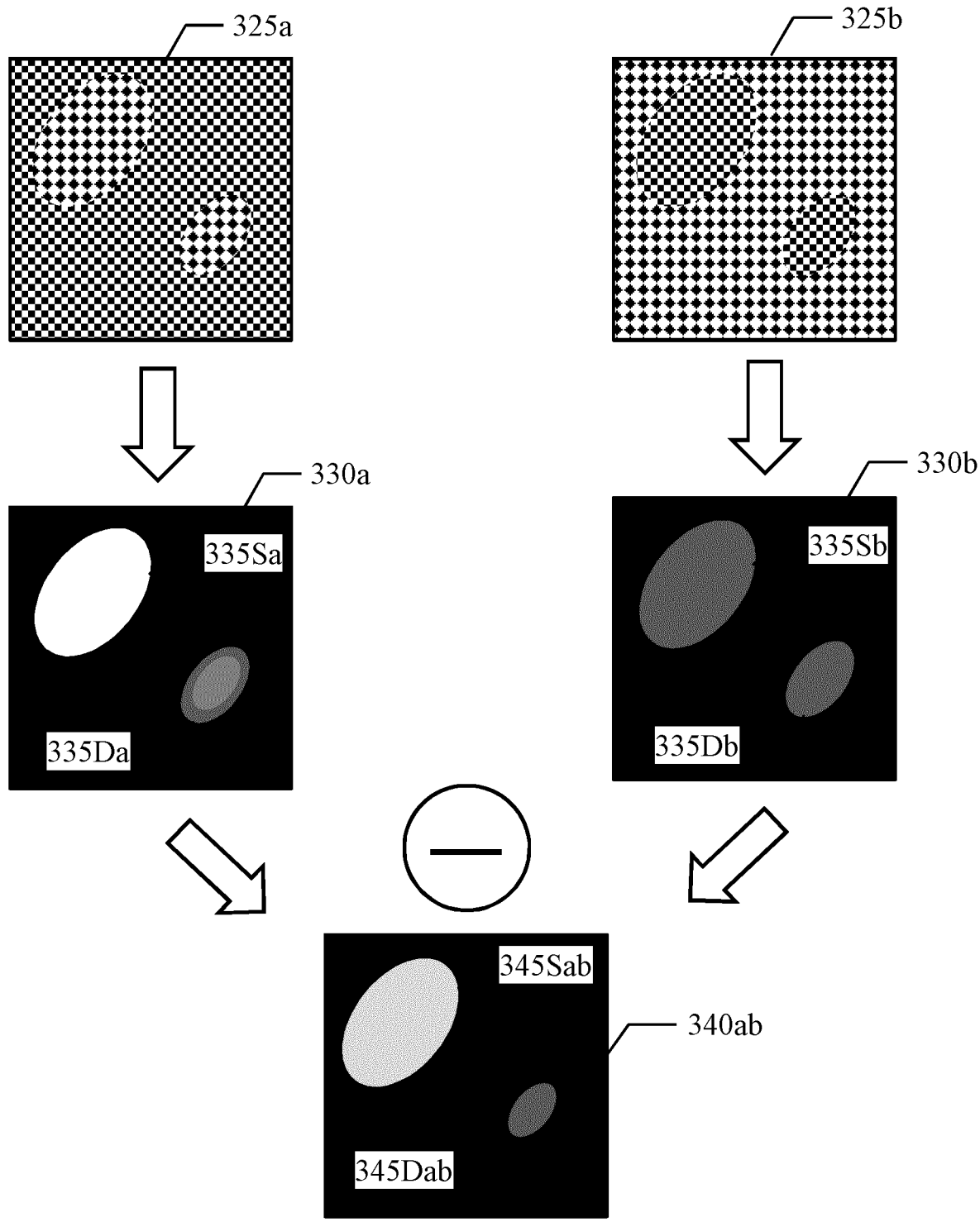

Moving to FIG. 3B, in the solution according to an embodiment of the present disclosure a similar refining loop is performed for discriminating the superficial/deep target regions at different depths in the body-part (as above, working on a combined image which is initialized to the starting image). Particularly, a main partial illumination 325a is applied to the body-part. The main partial illumination 325a corresponds to a main spatial pattern providing a prevalent illumination (most white) of two regions of the body-part corresponding to the detection segments of the previous combined image and a prevalent non-illumination (most black) of a region of the body-part corresponding to a remaining non-detection segment of the previous combined image, to make the excitation light reach the corresponding locations of the body-part with a high spatial frequency and a low spatial frequency, respectively. A main component (fluorescence) image 330a is acquired in response to the main partial illumination 325a. The main component image 330a comprises two detection segments 335Sa and 335Da wherein the fluorescence light is detected, corresponding to the superficial target region and to the deep target region, respectively. The tissues act as a spatial low-pass filter, with filtering effectiveness increasing with thickness. Therefore, the high spatial frequency of the illumination of the superficial target region leaves the detection segment 335Sa substantially unaffected (white); conversely, the high spatial frequency of the illumination of the deep target region makes the detection segment 335Da significantly fade in a central portion thereof (light gray) and still more in a border portion thereof wherein the scattering is lower (dark gray). Moreover, a secondary partial illumination 325b is applied to the body-part. The secondary partial illumination 325b corresponds to a secondary spatial pattern which is the negative of the main spatial pattern of the main partial illumination 325a, providing a prevalent non-illumination (most black) and a prevalent illumination (most white) of the regions of the body-part corresponding to the detection segments and to the non-detection segment, respectively, of the previous combined image. A secondary component (fluorescence) image 330b is acquired in response to the secondary partial illumination 325b. The secondary component image 330b comprises two detection segments 335Sb and 335Db wherein the fluorescence light is detected, corresponding to the superficial target region and to the deep target region, respectively. Because of the low spatial frequency of the illumination of the (superficial/deep) target regions, both the detection segments 335Sb and 335Db are very faded (dark gray). The main component image 330a and the secondary component image 330b are combined into a (new version of the) combined image 340ab by subtracting them for each location of the body-part. As a result, the combined image 340ab has two detection segments 345Sab and 345Dab (wherein the fluorescence light is detected). The detection segment 345Sab, corresponding to the superficial target region, still represents it with a negligible fading (almost white). The detection segment 345Dab, corresponding to the deep target region, instead significantly fades in the central portion of the detection segment 335Da (dark gray) and disappears in the border portion of the detection segment 335Da (black). As a result, the detection segment 345Dab becomes smaller.

Figure 3C:
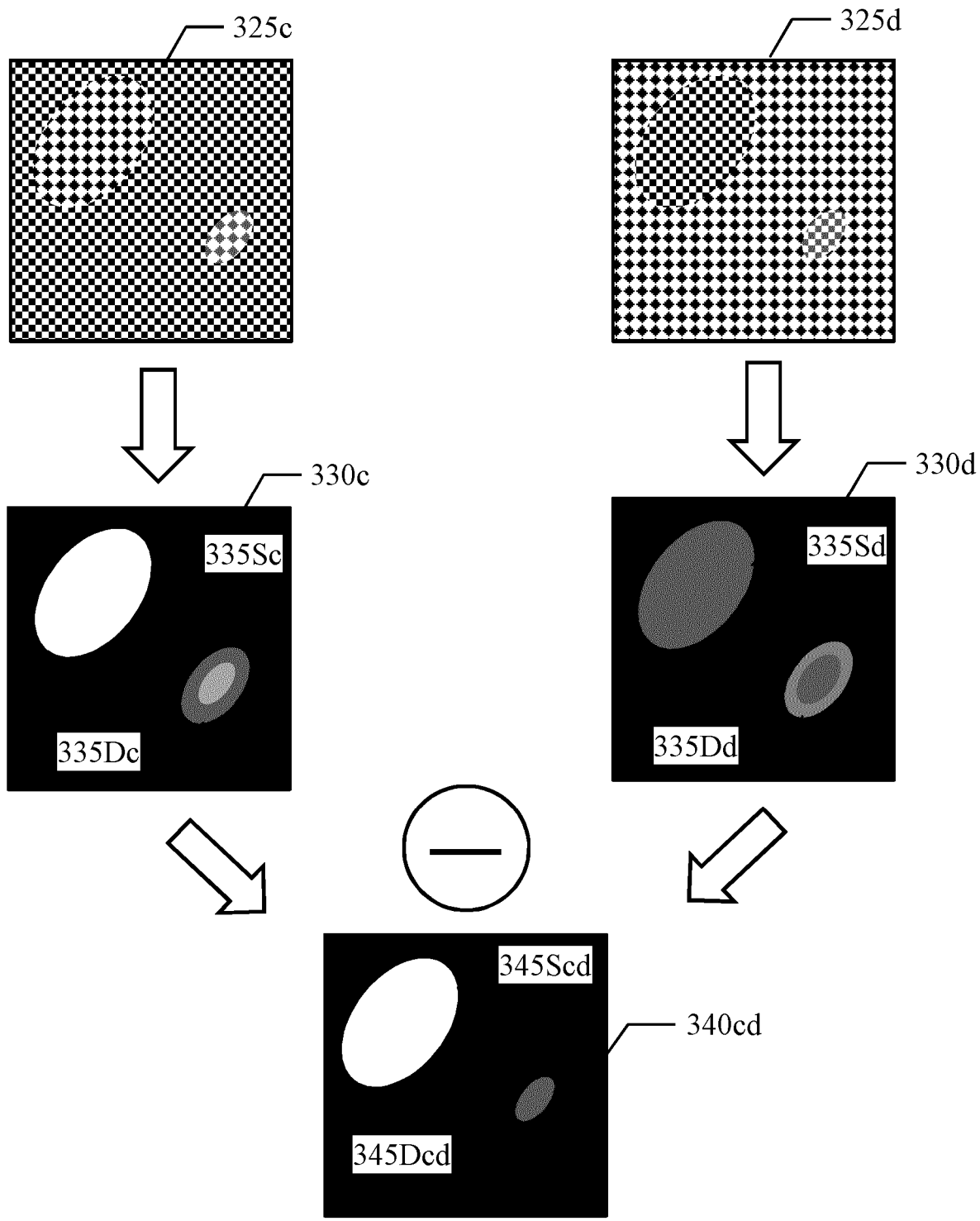

Moving to FIG. 3C, the same operations are repeated at each iteration of the refining loop. Particularly, a main partial illumination 325c, with a main spatial pattern defined according to the previous combined image, is applied to the body-part. A main component (fluorescence) image 330c, comprising two detection segments 335Sc,335Dc wherein the fluorescence light is detected, is acquired in response to the main partial illumination 325c. As above, the detection segment 335Sc, corresponding to the superficial target region, is substantially unaffected (white). Instead, because the detection segment has become smaller, now an inner portion of the deep target region receives the prevalent illumination and an outer portion of the deep target region receives the prevalent non-illumination. Therefore, as above a corresponding inner portion of the detection segment 335Dc significantly fades in a central portion thereof (light gray) and still more in a border portion thereof (dark gray); moreover, a corresponding outer portion of the detection segment 335Dc is very faded (dark gray). Moreover, a secondary partial illumination 325d, with a secondary spatial pattern being the negative of the main spatial pattern of the main partial illumination 325c, is applied to the body-part. A secondary component (fluorescence) image 330d, with two target regions 335Sd,335Dd wherein the fluorescence light is detected, is acquired in response to the secondary partial illumination 325d. As above, the detection segment 335Sd, corresponding to the superficial target region, is very faded (dark gray). Instead, again because the detection segment has become smaller, now the inner portion of the deep target region receives the prevalent non-illumination and the outer portion of the deep target region receives the prevalent illumination. Therefore, as above a corresponding inner portion of the detection segment 335Dd is very faded (dark gray), whereas a corresponding outer portion of the detection segment 335Dd is less faded (light gray). The main component image 330c and the secondary component image 330d are combined into a (new version of the) combined image 340cd, by subtracting them for each location of the body-part. As a result, the combined image 340cd has two detection segments 345Scd and 345Dcd corresponding to the superficial target region and to the deep target region, respectively. As above, the detection segment 345Scd still represents the superficial target region (with a negligible fading) and the detection segment 345Dcd (in the inner portion of the detection segment 335Dc) significantly fades in its central portion (dark gray) and disappears in its border portion (black); moreover, the detection segment 345Dcd disappears in the outer portion of the detection segment 335Dc as well (black). As a result, the detection segment 345Dcd again becomes smaller.

Figure 3D:
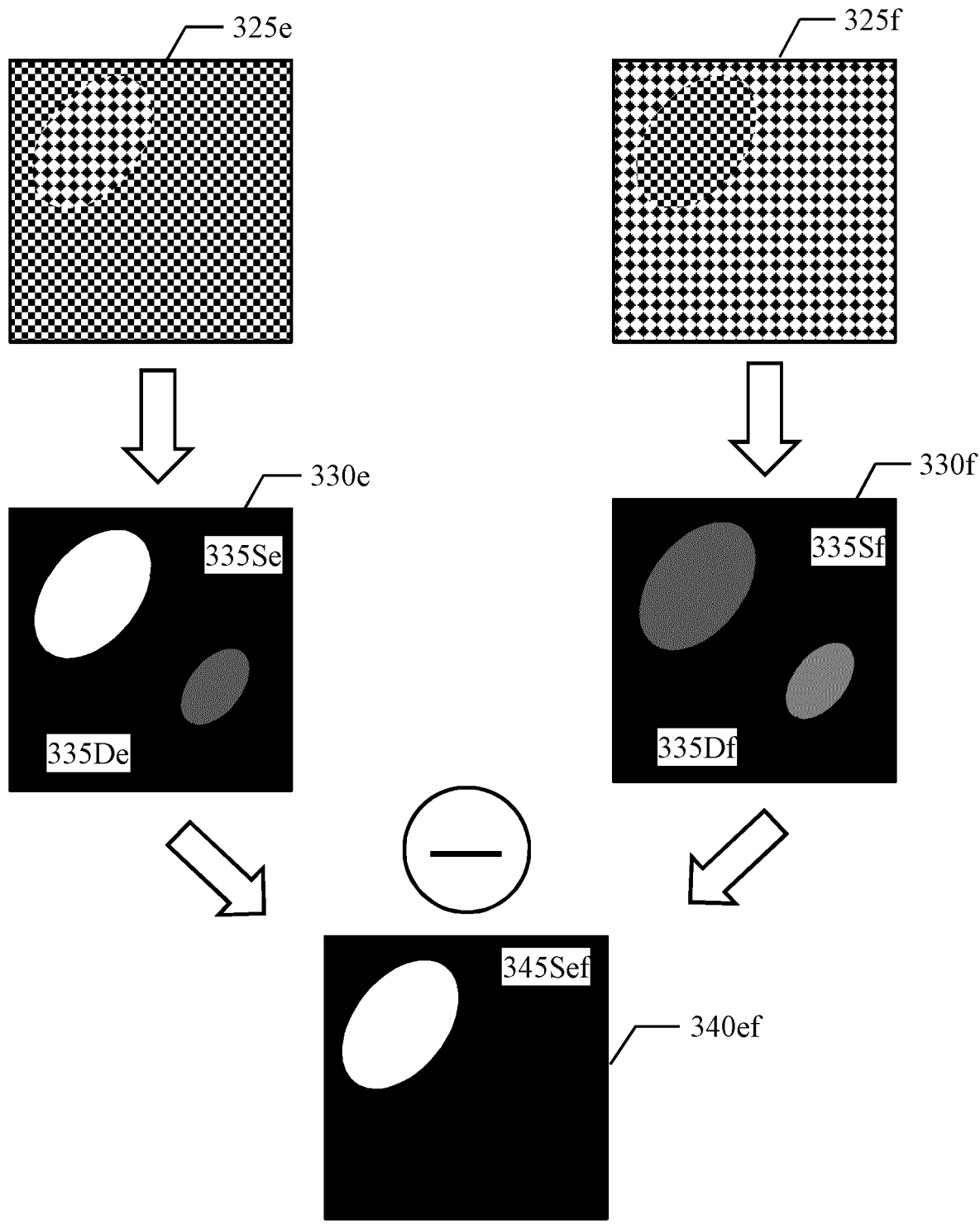

Moving to FIG. 3D, at a certain point the detection segment of the combined image corresponding to the deep target region disappears. Therefore, at a next iteration of the refining loop a main partial illumination 325e is applied to the body-part. The main partial illumination 325e corresponds to a main spatial pattern providing a prevalent illumination (most white) of a single region of the body-part corresponding to the single detection segment of the previous combined image (corresponding to the superficial target region) and a prevalent non-illumination (most black) of a remaining region of the body-part. A main component (fluorescence) image 330e, comprising two detection segments 335Se,335De wherein the fluorescence light is detected, is acquired in response to the main partial illumination 325e. As above, the detection segment 335Se, corresponding to the superficial target region, is substantially unaffected (white); instead, the prevalent non-illumination of the deep target region makes the detection segment 335De very faded (dark gray). Moreover, a secondary partial illumination 325f, with a secondary spatial pattern being the negative of the main spatial pattern of the main partial illumination 325e, is applied to the body-part. A secondary component (fluorescence) image 330f, with two detection segments 335Sf,335Df wherein the fluorescence light is detected, is acquired in response to the secondary partial illumination 325f. As above, the detection segment 335Sf, corresponding to the superficial target region, is very faded (dark gray). Instead, the prevalent illumination of the deep target region makes the detection segment 335Df less faded (light gray). The main component image 330e and the secondary component 330f are combined into a (new version of the) combined image 340ef, by subtracting them for each location of the body-part. The component image 340ef still has a single detection segment 345Sef corresponding to the superficial target region (representing it with a negligible fading), with the detection segment 335De corresponding to the deep target region that still disappears. The combined image then remains the same with only the detection segment representing the superficial target region.

Figure 3E:
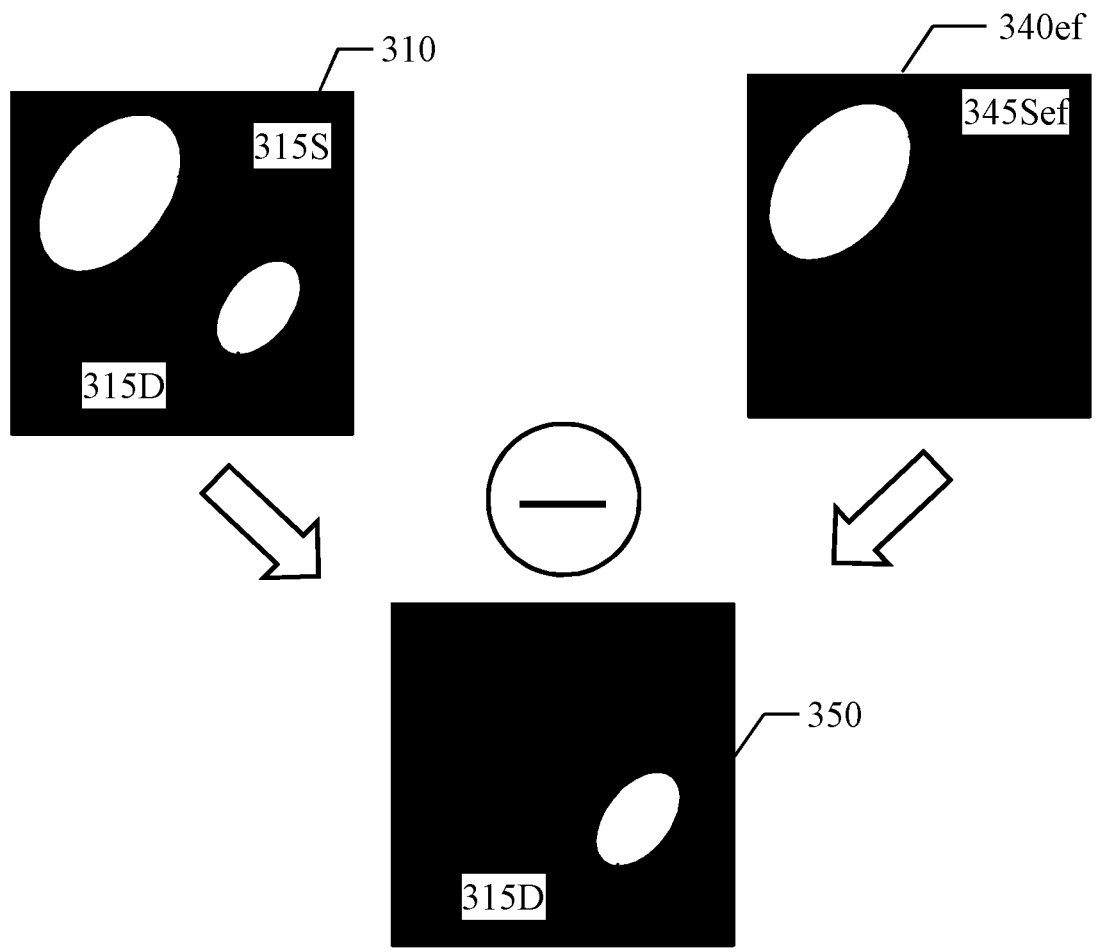

Moving to FIG. 3E, if necessary it is also possible to subtract the (last version of the) combined image 345Sef from the starting image 310. In a corresponding reversed (fluorescence) image 350 so obtained, the detection segment 345Sef corresponding to the superficial target region disappears; therefore, the reversed image 350 only has the detection segment 315D which represents the deep target region.

The above-described solution significantly improves the quality of the imaging. Particularly, in this way it is possible to reduce the diffusion of the representations of the target regions containing the fluorescence agent and/or to discriminate the representations of the target regions at different depths. All of the above facilitates the detection of the target regions in the body-parts. Particularly, in diagnostic applications this improves the identification and/or the quantification of the corresponding lesions and then reduces misinterpretations (with lower risk of false positives/negatives and wrong follow-up), in therapeutic applications this improves the delineation of the corresponding lesions to be treated (with lower risk of reduced effectiveness of a therapy or of damages to healthy tissues), in surgical applications this makes the recognition of the margins of lesions more precise (with lower risk of incomplete resection of the lesions or excessive removal of healthy tissues).

Figure 4:
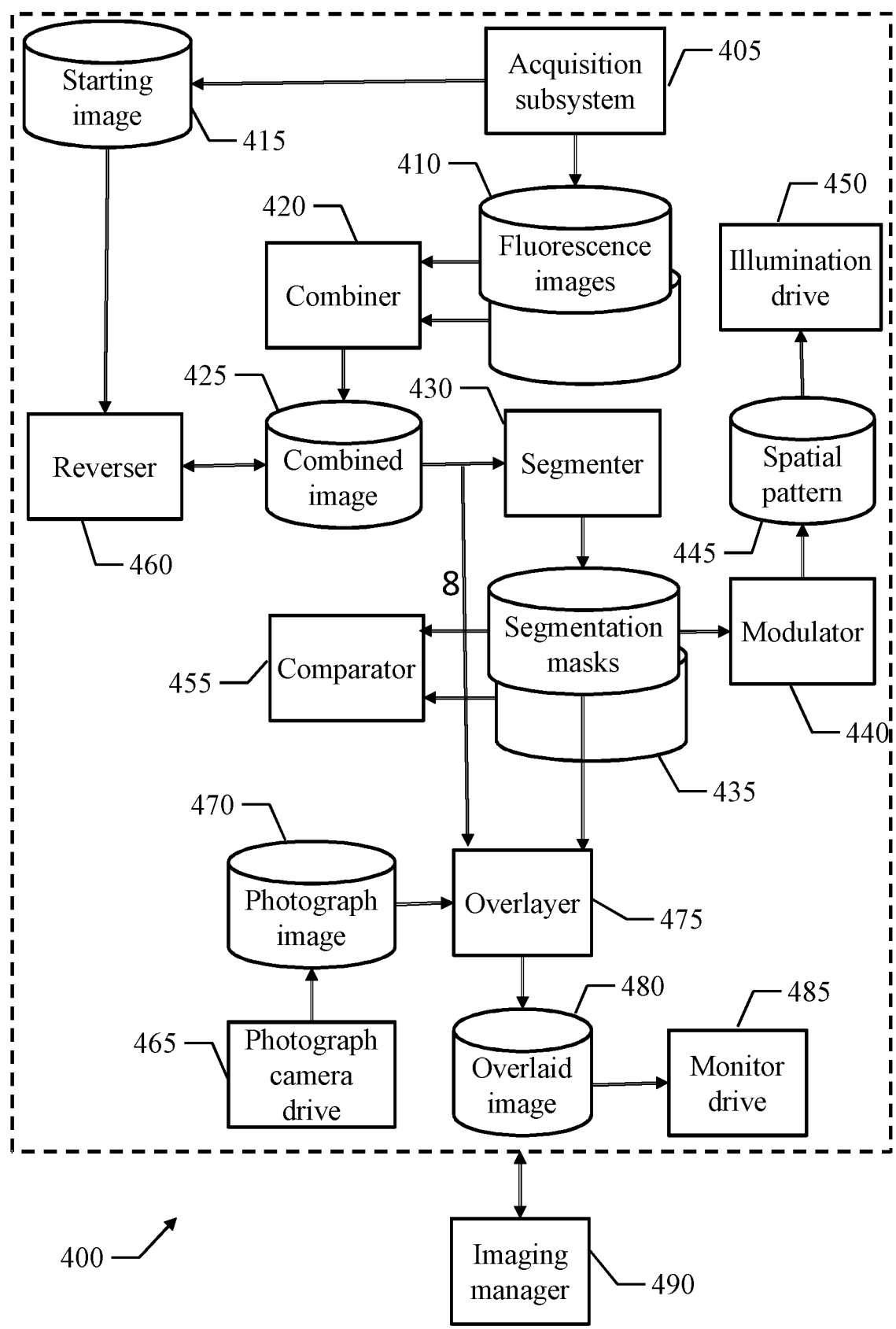
FIG. 4 shows the main software components that may be used to implement the solution according to an embodiment of the present disclosure.

With reference now to FIG. 4, the main software components are shown that may be used to implement the solution according to an embodiment of the present disclosure.

All the software components (programs and data) are denoted as a whole with the reference 400. The software components 400 are typically stored in the mass memory and loaded (at least in part) into the working memory of the control unit of the imaging system when the programs are running, together with other software components not directly relevant to the solution according to an embodiment of the present disclosure (such as an operating system, a user-interface module, a qualitative/quantitative analyzer and so on), which other software components are omitted for the sake of simplicity. The programs are initially installed into the mass memory, for example, from removable storage units or from the network (not shown in the figure). In this respect, each program may be a module, segment or portion of code, which comprises one or more executable instructions for implementing the specified logical function.

Particularly, an acquisition subsystem 405 drives acquisition components of the imaging probe (i.e., its emission filter and fluorescence camera) dedicated to acquiring the fluorescence images in succession (defining the starting image and the main/secondary component images) during each imaging process of the body-part. The acquisition subsystem 405 accesses (in write mode) a fluorescence image stack 410. The fluorescence image stack 410 is organized as a first-in-first-out (FIFO) shift register with two locations (tail and head) for storing the two last fluorescence images. Each fluorescence image is defined by a bitmap comprising a matrix of cells (for example, with 512 rows and 512 columns) each storing a value of a pixel, i.e., a basic picture element corresponding to a location of the body-part; each pixel value defines the brightness of the pixel as a function of the intensity of the fluorescence light emitted by the location (for example, coded on 16 bits, increasing from 0 (black) to $2^{16}-1$ (white) as the intensity of the fluorescence light increases). The acquisition subsystem 405 further accesses (in write mode) a starting image file 415. The starting image file 415 latches the starting image of the imaging process. A combiner 420 combines each pair of (main/secondary) component images, resulting from a pair of complementary (main/secondary) partial illuminations, into the corresponding combined image. The combiner 420 accesses (in read mode) both the tail and the head of the fluorescence image stack 410 and it accesses (in write mode) a combined image file 425. The combined image file 425 stores the last combined image. The combined image is defined by a bitmap comprising a matrix of cells with the same size as the fluorescence images each storing a pixel value for the corresponding location (derived from its pixel values of the pair of component images).

A segmenter 430 segments each combined image into one or more detection segments representing corresponding detection regions of the body-part wherein the fluorescence agent is detected (high brightness) and one or more non-detection segments representing corresponding non-detection regions of the body-part wherein the fluorescence agent is not detected (low brightness). The segmenter 430 accesses (in read mode) the combined image file 425 and it accesses (in write mode) a segmentation mask stack 435. The segmentation mask stack 435 as well is organized as a FIFO shift register with two locations (tail and head) for storing segmentation masks defining the segmentation of the two last combined images. Each segmentation mask is formed by a matrix of cells with the same size as the fluorescence images, each storing a segmentation flag (i.e., a binary value) for the corresponding location of the body-part; the segmentation flag is asserted (for example, at the logic value 1) when the fluorescence agent is detected in the location and it is deasserted (for example, at the logic value 0) when the fluorescence agent is not detected in the location. A modulator 440 determines each (starting/main/secondary) spatial pattern defining the corresponding (starting/main/secondary) illumination of the body-part. The modulator 440 accesses (in read mode) the tail of the segmentation mask file 435 (containing the last segmentation mask) and it accesses (in write mode) a spatial pattern file 445. The spatial pattern file 445 stores a spatial pattern mask defining the spatial pattern. The spatial pattern mask is formed by a matrix of cells with the same size as the fluorescence images, each storing an illumination flag for the corresponding location of the body-part; the illumination flag is asserted (for example, at the logic value 1) when the location is to be illuminated and it is deasserted (for example, at the logic value 0) when the location is not to be illuminated. An illumination drive 450 drives illumination components of the imaging probe (i.e., its light source and spatial modulator) dedicated to illuminating the body-part according to the spatial pattern. For this purpose, the illumination drive 450 accesses (in read mode) the spatial pattern file 445. A comparator 455 compares each pair of consecutive segmentation masks to determine a variation of the corresponding combined images. The comparator 455 accesses (in read mode) both the tail and the head of the segmentation mask stack 435. A reverser 460 reverses the discrimination of the target regions at different depths (from the superficial target regions to the deep target regions) in the last combined image resulting from the refining loop. For this purpose, the reverser 460 accesses (in read mode) the starting image file 415 and it accesses (in read/write mode) the combined image file 425 (containing the last combined image).

A photograph camera drive 465 drives the photograph camera of the imaging probe for acquiring the photograph images in succession during the imaging process. The photograph camera drive 465 accesses (in write mode) a photograph image file 470. The photograph image file 470 stores the last photograph image. The photograph image is defined by a bitmap comprising a matrix of cells (with a size either the same as or different from the one of the fluorescence images) each storing a pixel value for a corresponding location of the body-part (either the same or different with respect to the fluorescence images); each pixel value defines the brightness of the pixel as a function of the intensity of the (visible) light reflected by the corresponding location (for example, coded on 12 bits increasing from 0 (black) to $2^{12}-1$ (white) as the intensity of the reflected light increases in a gray scale representation). The photographic camera may be equipped with a pixel-interleaved spectral filter for different colors (such as red, green and blue for a Bayer-Patterned filter). In this case, the image in a following step is de-interlaced to interpolate each pixel value (in this tri-colored implementation: red, green and blue). For the tri-colored implementation, the photographic image is stored accordingly in a tri-colored representation.

An overlayer 475 generates overlaid images in succession during the imaging process each according to a corresponding set of last combined image, segmentation mask and photograph image. The overlayer 475 accesses (in read mode) the combined image file 425 (containing the last combined image), the tail of the segmentation mask stack 435 (containing the corresponding last segmentation mask) and the photograph image file 470 (containing the last photograph image), and it accesses (in write mode) an overlaid image repository 480. The overlaid image repository 480 stores a sequence of the overlaid images that are generated during the imaging process. Each overlaid image is defined by a bitmap comprising a matrix of cells (with the same size of the fluorescence images, the same size of the photograph image or a size different from both of them), each storing a pixel value for a corresponding location of the body-part (either the same or different with respect to the fluorescence images and the photograph image), obtained by overlaying the combined image processed according to the segmentation mask onto the photograph image (as described in the following). A monitor drive 485 drives the monitor of the central unit for displaying the overlaid images in succession. The monitor drive 485 accesses (in read mode) the overlaid image repository 480.

An imaging manager 490 manages the imaging process. For this purpose, the imaging manager 490 interfaces with the above-mentioned software modules.

Figure 5A:
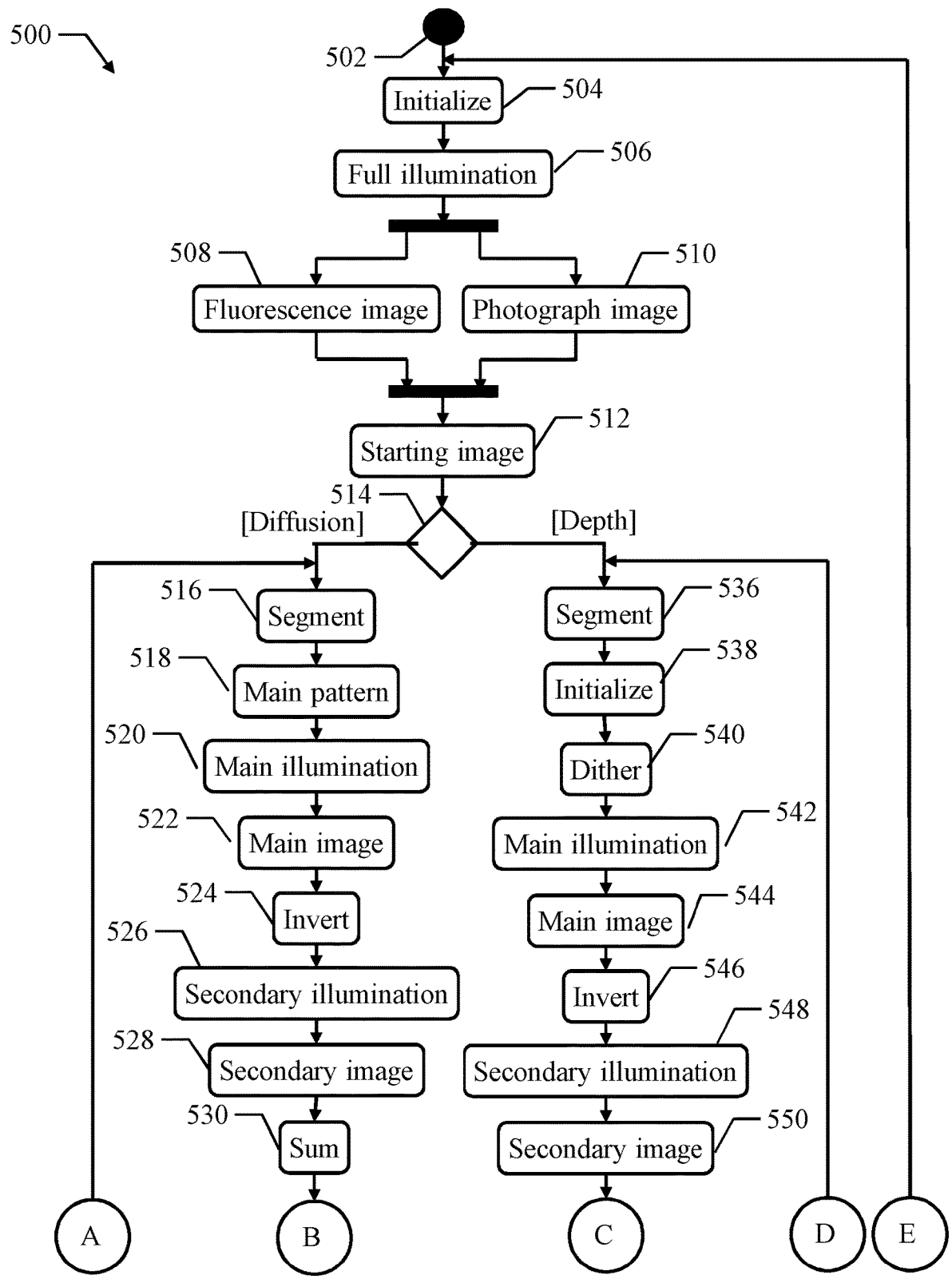
FIG. 5A-FIG. 5B show an activity diagram describing the flow of activities relating to an implementation of the solution according to an embodiment of the present disclosure.
Figure 5B:
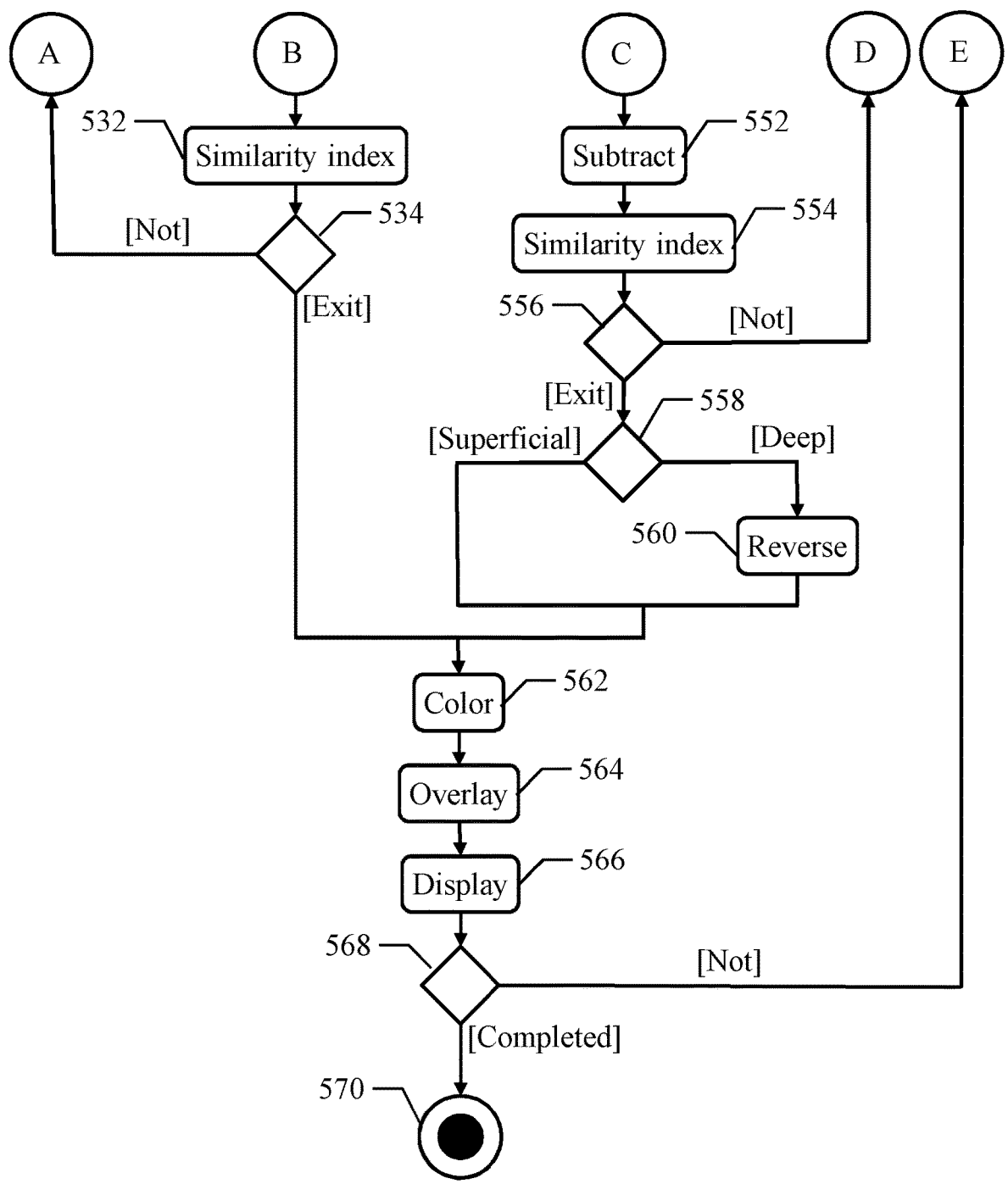

With reference now to FIG. 5A-FIG. 5B, an activity diagram is shown describing the flow of activities relating to an implementation of the solution according to an embodiment of the present disclosure.

Particularly, the activity diagram represents an exemplary process that may be used to image the body-part with a method 500. In this respect, each block may correspond to one or more executable instructions for implementing the specified logical function on the control server.

Before an imaging process of the body-part, a health care professional (for example, a nurse or a medical doctor) administers a fluorescence agent to the patient (an administration time is decided depending on the pharmacokinetics of the fluorescence agent). For example, the fluorescence agent is a target-specific fluorescence agent which is adapted to attaching to a specific (biological) target by means of a specific interaction therewith. The desired behavior may be achieved by incorporating a target-specific ligand into the formulation of the fluorescence agent, for example, based on chemical binding properties and/or physical structure adapted to interacting with different tissues, vascular properties, metabolic characteristics and so on. For example, in oncologic (diagnostic/therapeutic/surgical) applications, the fluorescence agent may be target-specific for tumoral tissues. As another example, in any surgical applications the fluorescence agent may be target-specific for vital tissue which should be preserved in surgical interventions, such as nerves, blood-vessels, lymph-nodes or lymph-vessel. The fluorescence agent is administered to the patient intravenously as a bolus (with a syringe); as a consequence, the contrast agent circulates within the vascular system of the patient until reaching the body-part and binding to the desired target (such as by interaction therewith at molecular level). Unbound fluorescence agents is instead cleared from the blood pool according to the corresponding blood half-life time and therefore washed out of the body-part. The timing of these processes depends on multiple parameters and it may be influenced by the chemical properties of the targeted agent (for example, in case of target-specific fluorescent agent for humanized antibodies, a sufficient administration time was shown to be in the order of 24-72 hours before the imaging process). At the time of the imaging process (i.e., a diagnostic examination, a therapeutic treatment or a surgical intervention), the imaging probe is placed close to the body-part. An operator of the imaging system (for example, a radiologist or a surgeon) then enters a start command into the central unit to start imaging the body-part.

In response thereto, the imaging manager starts the imaging process by passing from the black start circle 502 to block 504. At this point, the modulator defines the starting spatial pattern for providing the starting illumination of the body-part. For this purpose, the modulator generates a new spatial pattern mask by asserting the illumination flags of all the locations. As a result, the starting spatial pattern is configured to provide a full illumination (i.e., forwarding the illumination provided by the light source) to all the locations of the body-part. The modulator saves the spatial pattern mask so obtained into the corresponding file (by replacing its previous version). The illumination drive at block 506 applies the starting illumination corresponding to the spatial pattern mask extracted from the corresponding file; in this case, the illumination drive causes the excitation light to reach all the locations of the body-part. The flow of activity then forks into two operations that are performed concurrently. Particularly, the acquisition subsystem at block 508 acquires a new fluorescence image, defining the starting image. The fluorescence camera drive adds the starting image so obtained to the fluorescence image stack (saving it into the tail after shifting its content to the head whose content is lost); moreover, the acquisition subsystem also saves the starting image into the corresponding file (to avoid loosing it during the next refining loop). At the same time, the photograph camera drive at block 510 acquires a new photograph image. The photograph camera drive saves the photograph image into the corresponding file (by replacing its content). The flow of activity joints at block 512, wherein the combiner initializes the combined image by saving the starting image (extracted from the tail of the fluorescence image stack) into the corresponding file (by replacing its content).

The process now branches at block 514 according to a configuration of the imaging system (for example, indicated in a preset parameter with the possibility of changing it at runtime together with the start command). Particularly, if the imaging system is configured for reducing the diffusion of the target regions the blocks 516-534 are executed, whereas if the imaging system is configured for discriminating the target regions at different depths the blocks 536-560 are executed. In both cases, the method then merges again at block 562.

Considering now the block 516 (configuration for reducing the diffusion of the target regions), the corresponding refining loop is entered. At this point, the segmenter retrieves the last combined image from the corresponding file (consisting of the starting image at the beginning). The segmenter then segments the combined image into one or more detection segments and one or more non-detection segments. For example, the locations of the body-part are classified by assigning each of them to one of two classes, i.e., a detection class for (detection) locations wherein the fluorescence agent is detected and a non-detection class for (non-detection) locations wherein the fluorescence agent is not detected. Particularly, each location is assigned to the detection class or to the non-detection class when its pixel value is (possibly strictly) higher or lower, respectively, than a segmentation threshold. The segmentation threshold may be calculated to maximize an intra-class variance between the pixel values of the locations assigned to the two (detection/non-detection) classes (such as by applying the Otsu's algorithm). The detection segments and non-detection segments are then defined by clustering the locations into substantially homogenous groups of detection locations and non-detection locations, respectively (such as by applying the k-nearest-neighbors (kNN) algorithm). The segmenter generates a new segmentation mask by asserting or de-asserting the segmentation flag of each location assigned to a detection segment or to a non-detection segment, respectively. The segmenter adds the segmentation mask so obtained to the corresponding stack (saving it into the tail after shifting the previous segmentation mask to the head whose content is lost).

The modulator at block 518 determines the main spatial pattern corresponding to the segmentation mask (extracted from the tail of the corresponding stack). For this purpose, the modulator generates a new spatial pattern mask by simply copying the segmentation mask, so that the illumination flag of each location is asserted or deasserted when the location belongs to a detection segment or to a non-detection segment, respectively. As a result, the main spatial pattern is configured to provide a full illumination (i.e., forwarding the illumination provided by the light source) to the locations of the body-part corresponding to the detection segments and a non-illumination (i.e., blocking the illumination provided by the light source) to the locations of the body-part corresponding to the non-detection segments. The modulator saves the spatial pattern mask so obtained into the corresponding file (by replacing its content). The illumination drive at block 520 applies the main partial illumination corresponding to the spatial pattern mask (extracted from the corresponding file); in this case, the main spatial pattern causes the excitation light to reach only the locations of the body-part corresponding to the detection segments. The acquisition subsystem at block 522 acquires a new fluorescence image, defining the corresponding main component image. The acquisition subsystem adds the main component image so obtained to the fluorescence image stack (as above). The modulator at block 524 determines the secondary spatial pattern, defining the secondary partial illumination (complementary of the previous main partial illumination). For this purpose, the modulator generates a new spatial pattern mask by simply inverting the one stored in the corresponding file (exchanging its logic values 0 and 1). The modulator saves the spatial pattern mask so obtained into the corresponding file (as above). The illumination drive at block 526 applies the secondary partial illumination corresponding to the spatial pattern mask (extracted from the corresponding file); in this case, the secondary spatial pattern causes the excitation light to reach only the locations of the body-part corresponding to the non-detection segments. The acquisition subsystem at block 528 acquires a new fluorescence image, defining the corresponding secondary component image. The acquisition subsystem adds the secondary component image so obtained to the fluorescence image stack (as above); as a result, the fluorescence image stack will contain the pair of (main/secondary) component images corresponding to the pair of complementary (main/secondary) partial illuminations applied to the body-part.

The combiner at block 530 extracts the pair of component images from the head and tail of the corresponding stack. The combiner generates a new combined image by summing the component images pixel-by-pixel (for each location, with the pixel value of the combined image set to the pixel value of the main component image extracted from the head plus the pixel value of the secondary component image extracted from the tail). The combiner saves the combined image so obtained into the corresponding file (as above). Starting from a second iteration of the refining loop, the comparator at block 532 extracts the two last segmentation masks from the head and the tail of the corresponding stack, defining the segmentation of the two last combined images. The comparator calculates a similarity index which measures a similarity between the segmentation masks (and then between the corresponding combined images as well); for example, the similarity index is defined by the Sorensen-Dice coefficient, as twice the number of locations having the same segmentation flag in the segmentation masks divided by the total number of locations (ranging from 0 to 1 in increasing order of similarity). The comparator at block 534 verifies an exit condition of the refining loop, defined according to the similarity index. Particularly, if the similarity index is (possibly strictly) lower than a similarity threshold (for example, 0.8-0.9), meaning that the combined image is still refining significantly, the refining loop is iterated by returning to the block 516 (always true at a first iteration of the refining loop). Conversely, meaning that the combined image has reached a substantial stable refinement, the refining loop is exit by descending into block 566.

Considering now the block 536 (configuration for discriminating the target regions at different depth), the corresponding refining loop is entered. As above, the segmenter retrieves the last combined image from the corresponding file (consisting of the starting image at the beginning), segments it (into its detection segments and non-detection segments), generates a corresponding new segmentation mask and adds it to the corresponding stack. At this point, the modulator determines the main spatial pattern corresponding to the segmentation mask (extracted from the tail of the corresponding stack). For this purpose, the modulator at block 538 initializes the main spatial pattern as above generating a new spatial pattern mask by simply copying the segmentation mask. The modulator at block 540 dithers (for example, by applying the Floyd-Steinberg algorithm) the main spatial pattern mask, so as to add a pseudo-random illumination noise to the main spatial pattern. As a result, the main spatial pattern is configured to provide a prevalent illumination of the locations of the body-part corresponding to the detection segments and a prevalent non-illumination of the locations of the body-part corresponding to the non-detection segments; the prevalent illumination distributes the illumination coming from the light source throughout the locations of the body-part corresponding to the detection segments with a high spatial frequency (for example, 70-90%) and the illumination coming from the light source throughout the locations of the body-part corresponding to the non-detection segments with a low spatial frequency, strictly lower than the high spatial frequency (for example, equal to 0.1-0.3 thereof, such as 10-30%). The modulator saves the spatial pattern mask so obtained into the corresponding file (as above). The illumination drive at block 542 applies the main partial illumination corresponding to the spatial pattern mask (extracted from the corresponding file); in this case, the spatial pattern causes the excitation light to reach mostly the locations of the body-part corresponding to the detection segments and barely the locations of the body-part corresponding to the non-detection segments. The acquisition subsystem at block 544 acquires a new fluorescence image, defining the corresponding main component image. The acquisition subsystem adds the main component image so obtained to the fluorescence image stack (as above). The modulator at block 546 determines the secondary spatial pattern, defining the secondary partial illumination (complementary to the previous main partial illumination). For this purpose, as above the modulator generates a new spatial pattern mask by simply inverting the one stored in the corresponding file (exchanging its logic values 0 and 1). The modulator saves the spatial pattern mask so obtained into the corresponding file (as above). The illumination drive at block 548 applies the secondary partial illumination corresponding to the spatial pattern mask (extracted from the corresponding file); in this case, the secondary spatial pattern causes the excitation light to reach barely the locations of the body-part corresponding to the detection segments and mostly the locations of the body-part corresponding to the non-detection segments. The acquisition subsystem at block 550 acquires a new fluorescence image, defining the corresponding secondary component image. The acquisition subsystem adds the secondary component image so obtained to the fluorescence image stack (as above), so that it contains the pair of (main/secondary) component images corresponding to the pair of complementary (main/secondary) partial illuminations applied to the body-part as above.

The combiner at block 552 extracts the pair of component images from the head and the tail of the corresponding stack. The combiner generates a new combined image by subtracting the component images pixel-by-pixel; more specifically, for each location, the pixel value of the combined image is set to the pixel value of the main component image extracted from the head minus the pixel value of the secondary component image extracted from the tail. The combiner saves the combined image so obtained into the corresponding file (as above). Starting from a second iteration of the refining loop, the comparator at block 546 extracts the two last segmentation masks from the head and the tail of the corresponding stack, defining the segmentation of the two last combined images, and it calculates their similarity index as above. The comparator at block 548 verifies the same exit condition of the refining loop (defined according to the similarity index). Particularly, if the similarity indicator is (possibly strictly) lower than the similarity threshold, the refining loop is iterated by returning to the block 536 (always true at a first iteration of the refining loop). Conversely, the refining loop is exit by descending into block 558.

At this point, the flow of activity branches according to the desired type of discrimination of the target regions at different depths. Particularly, if the imaging system is configured for discriminating the deep target regions (with respect to the superficial target regions), the reverser at block 560 extracts the starting image (acquired at the beginning of the refining loop) from the corresponding file and the last combined image (only representing the superficial target regions) from the tail of the corresponding stack. The reverser generates a reversed (version of the) combined image by subtracting the last (version of the) combined image from the starting image pixel-by-pixel; more specifically, for each location, the pixel value of the reversed combined image is set to the pixel value of the starting image minus the pixel value of the last combined image. The combiner saves the (reversed) combined image so obtained into the corresponding file (as above). The process then descends into the block 562; the same point is also reached directly from the block 558 if the imaging system is configured for discriminating the superficial target regions (with respect to the deep target regions), so as to leave the combined image unchanged. In both cases (not shown in the figure), at this point it is also possible to improve the representations of the (selected) superficial or deep target regions which have been selected to be discriminated by applying thereto the above-mentioned technique for reducing the diffusion. Particularly, for each selected target region a sub-image is extracted from a corresponding portion of the combined image (retrieved from the corresponding file), for example, by setting it to the smallest rectangle containing the representation of the selected target region. The same operations described above are then repeated for this sub-image, so as to restore the representation of the selected target region with reduced diffusion. The portion of the combined image from which the sub-image has been extracted is then replaced with the obtained result in the corresponding file.

With reference now to the block 562, the overlayer retrieves the (last) combined image from the corresponding file and its segmentation mask from the tail of the corresponding stack. The overlayer colors the combined image by converting the pixel value of each location, whose corresponding segmentation flag in the segmentation mask is asserted (i.e., wherein the fluorescence agent has been detected), into a discrete level and then associating it with a representation of a corresponding color (for example, by means of an access index to a palette), with the higher the discrete level the brighter the color. In this phase, it is also possible to apply any (advantageously monotonical) transfer function to adjust opacity. The overlayer at block 564 further retrieves the (last) photograph image from the corresponding file. The overlayer generates the overlaid image by superimposing the (colored) combined image onto the photograph image. For this purpose, if necessary the combined image and the photograph image are scaled to a common size and/or transposed to a common image-coordinate system, in a way that their corresponding pixel values originate from the same locations of the body-part. An affine transformation is an advantageous implementation of this transformation, whose parameters may be calculated in an image-calibration step before standard operation of the imaging system. For each location, the pixel value of the overlaid image is then set to the (color-coded) pixel value of the combined image when the corresponding segmentation flag in the segmentation mask is asserted (fluorescence agent being detected) or to the pixel value of the photograph image otherwise (fluorescence agent being not detected). The overlayer adds the overlaid image so obtained to the corresponding repository (at the end of the corresponding sequence). The monitor drive at block 566 extracts the overlaid images in succession from the corresponding repository and displays them onto the monitor (substantially in real-time, apart from a small delay caused by the refining loop). In this way, the overlaid images show the presence of the fluorescence agent (quantified according to the corresponding colors), contextualized on an anatomical representation of the body-part. For example, this information may be used in diagnostic applications to identify and/or quantify lesions (such as new lesions being discovered or known lesions being monitored), in therapeutic applications to delineate lesions to be treated (such as by applying radiations) or in surgical applications to recognize margins of lesions to be resected (guided surgery).

A test is made at block 568, wherein the imaging manager verifies whether the imaging process has been completed. If not, the flow of activity returns to the block 504 to repeat the same operations. Conversely, as soon as the operator has entered an end command of the imaging process into the central unit, the flow of activity descends into the concentric white/black stop circles 578.

Figure 6:
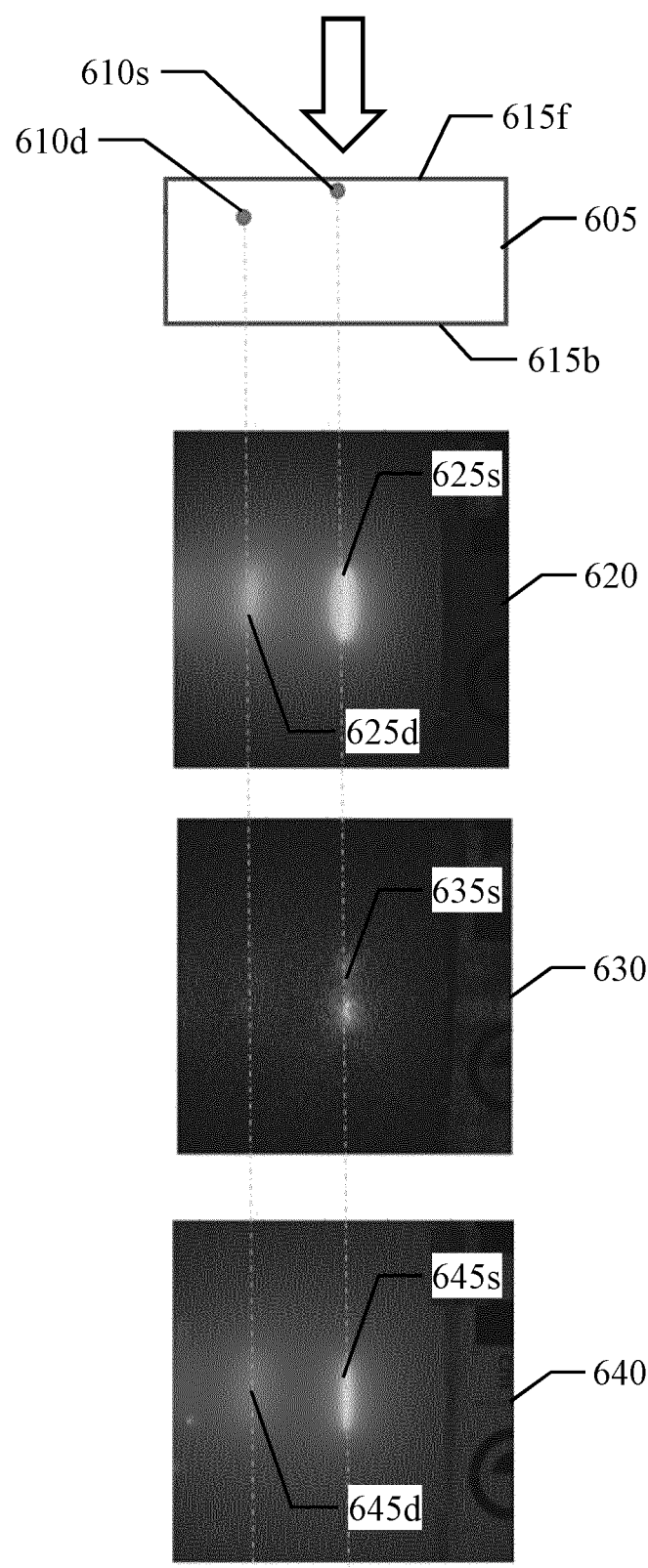
FIG. 6 shows an example of in-vitro application of the solution according to an embodiment of the present disclosure.

With reference now FIG. 6, an example is shown of in-vitro application of the solution according to an embodiment of the present disclosure.

An optical phantom 605 has been created to mimic optical properties (i.e., scattering and absorption) of biological tissues, for example, human breast tissues. The optical phantom 605 is based on a liquid contained in a box with transparent walls. The optical phantom 605 allows the introduction of (transparent) vials containing a fluorescence agent within it. Particularly, a superficial vial 610$s$ has been introduced superficially into the optical phantom 605 and a deep vial 610$d$ has been introduced deeply into the optical phantom 605, close to and far away from, respectively, a front surface 615$f$ of the optical phantom 605. The optical phantom 605 has then been imaged in different ways (with an epi-illumination geometry as above).

Particularly, the optical phantom 605 has been imaged by simply applying a full illumination. A fluorescence image 620 so obtained shows two (light) detection segments 625$s$ and 625$d$ which represent the superficial vial 610$s$ and the deep vial 610$d$, respectively. However, the detection segments 625$s$,625$d$ are relatively diffused; moreover, it is not possible to discriminate their different depths from the front surface 615$f$.

The optical phantom 605 has been imaged as indicated above for discriminating the target regions at different depths, and particularly the superficial target regions with respect to the deep target regions. A fluorescence image 630 so obtained only shows a (light) detection segment 635$s$ which represents the superficial vial 610$s$ (whereas no representation appears of the deep vial 610$d$).

The optical phantom 605 has been imaged as indicated above for reducing the diffusion of the target regions. A fluorescence image 640 so obtained shows two (light) detection segments 645$s$ and 645$d$ which represent the superficial vial 610$s$ and the deep vial 610$d$, respectively. The detection segment 645$s$ is far less diffused (whereas the detection segment 645$d$ is barely discernible).

Modifications

Naturally, in order to satisfy local and specific requirements, a person skilled in the art may apply many logical and/or physical modifications and alterations to the present disclosure. More specifically, although this disclosure has been described with a certain degree of particularity with reference to one or more embodiments thereof, it should be understood that various omissions, substitutions and changes in the form and details, as well as other embodiments, are possible. Particularly, different embodiments of the present disclosure may even be practiced without the specific details (such as the numerical values) set forth in the preceding description to provide a more thorough understanding thereof, conversely, well-known features may have been omitted or simplified in order not to obscure the description with unnecessary particulars. Moreover, it is expressly intended that specific elements and/or method steps described in connection with any embodiment of the present disclosure may be incorporated in any other embodiment as a matter of general design choice. Moreover, items presented in a same group and different embodiments, examples or alternatives are not to be construed as de facto equivalent to each other (but they are separate and autonomous entities). In any case, each numerical value should be read as modified according to applicable tolerances; particularly, the terms "substantially", "about", "approximately" and the like should be understood as "within 10%". Moreover, each range of numerical values should be intended as expressly specifying any possible number along the continuum within the range (comprising its end points). Ordinal or other qualifiers are merely used as labels to distinguish elements with the same name but do not by themselves connote any priority, precedence or order. The terms include, comprise, have, contain, involve and the like should be intended with an open, non-exhaustive meaning (i.e., not limited to the recited items), the terms based on, dependent on, according to, function of and the like should be intended as a non-exclusive relationship (i.e., with possible further variables involved), the term a/an should be intended as one or more items (unless expressly indicated otherwise), and the term means for (or any means-plus-function formulation) should be intended as any structure adapted or configured for carrying out the relevant function.

For example, an embodiment provides a method for imaging an object. However, the object may be of any type (for example, body-parts, fingerprints, mechanical parts, and so on) and it may be imaged for any purpose (for example, in medical analyses, forensic applications, defect/crack inspections, and so on).

In an embodiment, the object contains a luminescence substance. However, the luminescence substance may be of any extrinsic/intrinsic type (for example, any luminescence agent, any natural luminescence component, based on any luminescence phenomenon, such as fluorescence, phosphorescence, chemiluminescence, bio-luminescence, induced Raman-radiation, and so on) and it may be provided in any way (for example, administered in any way and at any time before and/or during the imaging, self-generated in any way, such as for fluorescence pigments deposited in the retinal pigment epithelium in case of age-related macular degeneration, and so on).

In an embodiment, the method is implemented under the control of a computing device. However, the computing device may be of any type (see below).

In an embodiment, the method comprises initializing (by the computing device) a combined image according to a starting imaging of the object or to default values. However, the combined image may be initialized in any way (for example, according to any starting imaging of the object, such as a fluorescence image thereof, a photograph image thereof and the like, according to any default values, such as all white, white in a selected region of interest and black elsewhere, and so on).

In an embodiment, the combined image comprises a plurality of image values representative of a luminescence light being emitted by the luminescence substance from corresponding locations of the object. However, the combined image may have any size and shape (from a whole matrix to one or more portions thereof), and it may comprise image values of any type (for example, pixel values, voxel values or groups thereof representing the corresponding locations of the object in any gray-scale or colors, and so on).

In an embodiment, the method comprises repeating (by the computing device) a refining loop until an exit condition of the refining loop is satisfied. However, the refining loop may be repeated until any exit condition is satisfied (such as depending on a result of each iteration, on a pre-defined maximum number of iterations, and so on).

In an embodiment, the refining loop comprises segmenting (by the computing device) the combined image into a plurality of segments representative of corresponding regions of the object according to a segmenting criterion based on the image values of the combined image. However, the combined image may be segmented in any number of segments (two or more for each of two or more classes, such as detection/non-detection segments, high-detection/low-detection/non-detection segments, and so on) and in any way (for example, by applying linear/quadratic classifiers, support vector machines, kernel estimators, decision trees, neural networks, and so on).

In an embodiment, the refining loop comprises determining (by the computing device) a plurality of spatial patterns. However, the spatial patterns may be in any number and of any type (for example, combining for providing a full illumination of the object, such as a pair of complementary spatial patterns, or more generally different to each other so as to excite specific spatial modes), and they may be determined in any way (for example, by calculating one spatial pattern of a pair of complementary spatial patterns and then inverting it to obtain the other one, by calculating all the spatial patterns directly, and so on).

In an embodiment, the plurality of spatial patterns are determined according to the segmentation of the combined image. However, the spatial patterns may be determined in any way according to the segmentation (for example, providing full illumination, non-illumination, prevalent illumination, prevalent non-illumination and so on in any combination).

In an embodiment, the refining loop comprises applying (by an illumination device) a plurality of partial illuminations corresponding to the spatial patterns to the object in succession. However, each partial illumination may be applied in any way (for example, in any scan mode, in full mode, and so on) by any illumination device (see below).

In an embodiment, the refining loop comprises acquiring (by an acquisition device), corresponding component images in response to the partial illuminations in succession. However, each component image may be acquired in any way (for example, in a single channel, in multiple channels, with any filtering, and so on) by any acquisition device (see below).

In an embodiment, each of the component images comprises corresponding image values representative of the locations of the object. However, each component image may have any size and shape, and it may comprise image values of any type (either the same or different with respect to the combined images).

In an embodiment, the refining loop comprises combining (by the computing device) the component images into a new version of the combined image. However, the component images may be combined in any way (for example, as is or compressed/expanded, by cumulating or differentiating the corresponding image values, by taking into account only the image values of the same location or of neighbor locations as well, and so on).

In an embodiment, the method comprises outputting (by an output device) an imaging result based on a last version of the combined image at an exit of the refining loop. However, the imaging result may be of any type (for example, an output image representing the object, a parametric image representing a distribution of a parameter value throughout the object, an aggregated value representing a property of a region of interest of the object, and so on) and it may be based on the last version of the combined image in any way (for example, as is or processed in any way, such as color-coded, and so on); moreover, the imaging result may be provided by any output device (see below).

Further embodiments provide additional advantageous features, which may however be omitted at all in a basic implementation.

Particularly, in an embodiment, the luminescence substance is a fluorescence substance. However, the fluorescence substance may be of any extrinsic/intrinsic type (for example, for imaging any pathological tissue, any healthy tissue, such as genetically encoded fluorophore expression like a fluorescence protein as green fluorescent protein (GFP) in pre-clinical applications, and so on).

In an embodiment, the method comprises applying (by the illumination device) a starting illumination to the object. However, the starting illumination may be of any other type (for example, a full illumination, a partial illumination, a structured illumination, and so on).

In an embodiment, the method comprises acquiring (by the acquisition device) a starting image in response to the starting illumination. However, the starting image may be acquired in any way (either the same or different with respect to the component images).

In an embodiment, the starting image comprises corresponding image values representative of the luminescence light being emitted by the luminescence substance from the locations of the object. However, the starting image may have any size and shape, and it may comprise image values of any type (either the same or different with respect to the combined image).

In an embodiment, the method comprises initializing (by the computing device) the combined image according to the starting image. However, the combined image may be initialized in any way according to the starting image (for example, as is or after any processing, and so on).

In an embodiment, the method comprises applying (by the illumination device) the starting illumination to the object providing a full illumination thereof. However, the full illumination may be of any type (for example, with any intensity, in scan/full mode, and so on).

In an embodiment, the method comprises segmenting (by the computing device) the combined image into at least one detection segment of the segments representative of a detection one of the regions (wherein the luminescence agent is detected) and at least one non-detection segment of the segments representative of a non-detection one of the regions (wherein the luminescence agent is not detected). However, the detection/non-detection segments may be of any number (either the same or different) and they may be determined in any way (for example, with any segmentation algorithms, such as based on thresholds determined dynamically or pre-defined, with any clustering algorithms, such as based on centroid or density models, histogram, edge-detection, region-growing or model-based algorithms, and so on).

In an embodiment, the method comprises determining (by the computing device) a main one of the spatial patterns for providing a full illumination of said at least one detection region and a non-illumination of said at least one non-detection region. However, the full illumination and the non-illumination of the main spatial pattern may be of any type (for example, uniform to provide sharp transitions, reducing towards the border of the detection region and the non-detection region, respectively, to provide a slow-gradient transition between them, and so on).

In an embodiment, the method comprises determining (by the computing device) a secondary one of the spatial patterns for providing a non-illumination of said at least one detection region and a full illumination of said at least one non-detection region. However, the full illumination and the non-illumination of the secondary spatial pattern may be of any type (either the same or different with respect to the main spatial pattern).

In an embodiment, the method comprises combining (by the computing device) the component images into the combined image by cumulating the corresponding image values of the component images into each image value of the combined image. However, the image values may be cumulated in any way (for example, according to their sum, product, integral, with or without time-dependent smoothing weights, and so on).

In an embodiment, the method comprises combining (by the computing device) the component images into the combined image by setting each image value of the combined image according to a sum of the corresponding image values of the component images. However, the image values may be summed in any way (for example, as is, weighted, and so on).

In an embodiment, the method comprises determining (by the computing device) a main one of the spatial patterns for providing a prevalent illumination distributed throughout said at least one detection region. However, the main spatial pattern may provide any prevalent illumination of the detection region (for example, by alternating illumination and non-illumination, by varying the intensity of the illumination, with a random distribution, with a uniform distribution, with an illumination reducing towards the border to provide a slow-gradient transition, and so on), with any type of illumination of the non-detection region (for example, prevalent non-illumination, non-illumination, and so on).

In an embodiment, the method comprises determining (by the computing device) a secondary one of the spatial patterns for providing a prevalent illumination distributed throughout said at least one non-detection region. However, the secondary spatial pattern may provide any prevalent illumination of the non-detection region (either the same or different with respect to the prevalent illumination of the detection region in the main spatial pattern), with any type of illumination of the detection region (for example, prevalent non-illumination, non-illumination, and so on).

In an embodiment, the method comprises determining (by the computing device) the main spatial pattern for providing a prevalent non-illumination distributed throughout said at least one non-detection region. However, the main spatial pattern may provide any prevalent non-illumination of the non-detection region (for example, by alternating illumination and non-illumination, by varying the intensity of the illumination, with a random distribution, with a uniform distribution, with an illumination increasing towards the border to provide a slow-gradient transition, and so on), with any type of illumination of the detection region (for example, prevalent illumination, full illumination, and so on).

In an embodiment, the method comprises determining (by the computing device) the secondary spatial pattern for providing a prevalent non-illumination distributed throughout said at least one detection region. However, the secondary spatial pattern may provide any prevalent non-illumination of the detection region (either the same or different with respect to the prevalent non-illumination of the non-detection region in the main spatial pattern), with any type of illumination of the non-detection region (for example, prevalent illumination, full illumination, and so on).

In an embodiment, the prevalent illumination provides an illumination distributed randomly and the prevalent non-illumination provides a non-illumination distributed randomly. However, the random distributions may be of any type, either the same or different (for example, true random, pseudo-random, and so on), and they may be obtained in any way (for example, by adding an illumination noise to a full illumination and to a non-illumination, respectively, by generating them directly, and so on).

In an embodiment, the prevalent illumination provides an illumination with a high spatial frequency and the prevalent non-illumination provides an illumination with a low spatial frequency lower than the high spatial frequency. However, the high spatial frequency and the low spatial frequency may have any values (in either relative or absolute terms).

In an embodiment, the method comprises initializing (by the computing device) at least one of the spatial patterns for providing a full illumination of each one of the regions to be provided the prevalent illumination and for providing a non-illumination of each one of the regions to be provided the prevalent non-illumination. However, the initialization may be applied only to the main spatial pattern or to the secondary spatial pattern (when the other one is obtained by inversion), to both the main/secondary spatial patterns (when each of them is calculated directly) in any way (either the same or different with respect to above).

In an embodiment, the method comprises adding (by the computing device) a pseudo-random illumination noise to each of the spatial patterns being initialized. However, the pseudo-random illumination noise may be added in any way (for example, with any dithering algorithm, such as of patterning or ordered type, or more generally with any pseudo-random generator, such as of non-uniform or middle-square type, and so on).

In an embodiment, the method comprises combining (by the computing device) the component images into the combined image by differentiating the corresponding image value of the component image resulting from the main spatial pattern and the corresponding image value of the component image resulting from the secondary spatial pattern into each image value of the combined image. However, the image values may be differentiated in any way (for example, according to their difference, ratio, derivative, with or without time-dependent smoothing weights, and so on).

In an embodiment, the method comprises combining (by the computing device) the component images into the combined image by setting each image value of the combined image according to a difference between the corresponding image value of the component image resulting from the main spatial pattern and the corresponding image value of the component image resulting from the secondary spatial pattern. However, the image values may be subtracted in any way (for example, as is, weighted, and so on).

In an embodiment, the method comprises reversing (by the computing device) the last version of the combined image by setting each image value thereof according to a difference between the corresponding image value of the starting image and the corresponding image value of the last version of the combined image. However, the image values may be subtracted in any way (for example, as is, weighted, and so on); in any case, this operation may be performed to replace the last version of the combined image, to create an additional version of the combined image, or it may be omitted at all.

In an embodiment, the spatial patterns of each iteration of the refining loop combine to provide a full illumination of the object. However, the spatial patterns may combine in any way to provide the full illumination (for example, with the corresponding image values of each location providing full illumination or non-illumination, partial illuminations summing to the full illumination, and so on).

In an embodiment, the method comprises verifying (by the computing device) the exit condition according to the combined image. However, the exit condition may be verified in any way according to the combined image (for example, based on a similarity among consecutive versions, a changing rate, and so on).

In an embodiment, the method comprises verifying (by the computing device) the exit condition according to a similarity of a current version of the combined image resulting from a current iteration of the refining loop (different from a first iteration of the refining loop) with respect to at least one previous version of the combined image resulting from a previous iteration of the refining loop. However, the similarity may be defined in any way (for example, based on the index of Sorensen-Dice, Jaccard, Bray-Curti, Czekanowski, Steinhaus, Pielou, Hellinger, and so on) and it may be used in any way to verify the exit condition (for example, satisfied as soon as the similarity between the two last versions of the combined image reaches any threshold, when this is true for two or more consecutive iterations of the refining loop, and so on).

In an embodiment, the object is a body-part. However, the body-part may be of any type (for example, organs, such as liver, prostate or heart, regions, tissues and so on) and in any condition (for example, within a living being, within a dead body, extracted from a body, such as a sample of a biopsy, and so on).

In an embodiment, the boy-part is of a patient. However, the patient may be of any type (for example, a human being, an animal, and so on).

In an embodiment, a luminescence agent has been pre-administered to the body-part before performing the method. However, the luminescence agent may be of any type (for example, any targeted luminescence agent, such as based on specific or non-specific interactions, any non-targeted luminescence agent, and so on) and it may have been pre-administered in any way (for example, with a syringe, an infusion pump, and so on) and at any time (for example, in advance, immediately before performing the method, continuously during it, and so on). In any case, this is a data-processing method that may be implemented independently of any interaction with the patient; moreover, the luminescence agent may also be administered to the patient in a non-invasive manner (for example, orally for imaging the gastrointestinal tract, via a nebulizer into the airways or via topical spray application during a surgical intervention), or in any case without any substantial physical intervention thereon that would require professional medical expertise or entail any health risk for the patient (for example, intramuscularly). Although the method may facilitate the task of a physician, it only provides intermediate results that may help him/her but with the medical activity stricto sensu that is always made by the physician himself/herself.

A further embodiment provides another method for imaging an object. As above, in an embodiment the object contains a luminescence substance, in an embodiment the method is implemented under the control of a computing device and in an embodiment the method comprises repeating (by the computing device) a refining loop until an exit condition of the refining loop is satisfied.

In an embodiment, the refining loop comprises determining (by the computing device) a plurality of spatial patterns, with the spatial patterns that are pre-defined at a first iteration of the refining loop and are defined by applying a preset modification to a previous version thereof at each next iteration of the refining loop. However, the spatial patterns may be of any number and they may be determined in any way. For example, it is possible to start with two complementary spatial patterns providing a uniform illumination with a high spatial frequency (for reducing the diffusion) or with a low spatial frequency (for discriminating different depths); at each next iteration of the refining loop, for example, the spatial patterns are changed by reducing the high spatial frequency or by increasing the low spatial frequency (such as by a fixed percentage), by shifting them (such as by a fixed offset), and so on).

As above, in an embodiment the refining loop comprises applying (by an illumination device) a plurality of partial illuminations corresponding to the spatial patterns to the object in succession, in an embodiment the refining loop comprises acquiring (by an acquisition device) corresponding component images in response to the partial illuminations in succession, in an embodiment each of the component images comprises a plurality of image values representative of a luminescence light being emitted by the luminescence substance from corresponding locations of the object, in an embodiment the refining loop comprises combining (by the computing device) the component images into a new version of a combined image, in an embodiment the combined image comprises corresponding image values representative of the luminescence light being emitted by the luminescence substance from the locations of the object and in an embodiment the method comprises outputting (by an output device) an imaging result based on a last version of the combined image at an exit of the refining loop.

The same considerations pointed out above apply to this embodiment as well (for example, with reference to the additional features of the reversing of the last version of the combined image, to the exit condition of the refining loop, to the application to the body-part, and so on).

Generally, similar considerations apply if the same solution is implemented with an equivalent method (by using similar steps with the same functions of more steps or portions thereof, removing some steps being non-essential, or adding further optional steps); moreover, the steps may be performed in a different order, concurrently or in an interleaved way (at least in part).

An embodiment provides a computer program, which is configured for causing a computing device to perform the above-mentioned method when the computer program is executed on the computing device. An embodiment provides a computer program product, which comprises a computer readable storage medium embodying a computer program, the computer program being loadable into a working memory of a computing device thereby configuring the computing device to perform the same method. However, the computer program may be implemented as a stand-alone module, as a plug-in for a pre-existing software program (for example, the imaging manager) or even directly in the latter. In any case, similar considerations apply if the computer program is structured in a different way, or if additional modules or functions are provided; likewise, the memory structures may be of other types, or may be replaced with equivalent entities (not necessarily consisting of physical storage media). The computer program may take any form suitable to be used by any computing device (see below), thereby configuring the computing device to perform the desired operations; particularly, the computer program may be in the form of external or resident software, firmware, or microcode (either in object code or in source code—for example, to be compiled or interpreted). Moreover, it is possible to provide the computer program on any computer readable storage medium. The storage medium is any tangible medium (different from transitory signals per se) that may retain and store instructions for use by the computing device. For example, the storage medium may be of the electronic, magnetic, optical, electromagnetic, infrared, or semiconductor type; examples of such storage medium are fixed disks (where the program may be pre-loaded), removable disks, memory keys (for example, USB), and the like. The computer program may be downloaded to the computing device from the storage medium or via a network (for example, the Internet, a wide area network and/or a local area network comprising transmission cables, optical fibers, wireless connections, network devices); one or more network adapters in the computing device receive the computer program from the network and forward it for storage into one or more storage devices of the computing device. In any case, the solution according to an embodiment of the present disclosure lends itself to be implemented even with a hardware structure (for example, by electronic circuits integrated in one or more chips of semiconductor material), or with a combination of software and hardware suitably programmed or otherwise configured.

An embodiment provides a system, which comprises means configured for performing the steps of the above-mentioned method. An embodiment provides a system comprising a circuitry (i.e., any hardware suitably configured, for example, by software) for performing each step of the same method. However, the system may be of any type (for example, an imaging system, a microscope, a flexible-fiber-based endoscope (fiberscope), a rigid fiberscope, a flexible endoscope featuring an image digitalization on the distal end (videoscope), a rigid rod-lens-based laparoscope, and so on) and it may comprise any computing device (for example, any integrated central unit, any separate computer, and so on), any illumination device (for example, based on laser, LEDs, UV/halogen/Xenon lamp, and so on), any acquisition device (for example, based on any number and type of lenses, wave guides, mirrors, CCD, ICCD, EMCCD, CMOS, InGaAs or PMT sensors, and so on) and any output device (for example, a monitor, a printer, a network connection, a head-mounted video-projection device, and so on).

Generally, similar considerations apply if the system has a different structure or comprises equivalent components, or it has other operative characteristics. In any case, every component thereof may be separated into more elements, or two or more components may be combined together into a single element; moreover, each component may be replicated to support the execution of the corresponding operations in parallel. Moreover, unless specified otherwise, any interaction between different components generally does not need to be continuous, and it may be either direct or indirect through one or more intermediaries.

An embodiment provides a diagnostic method comprising the following steps. A body-part of the patient is imaged according to the above-mentioned method so as to output the corresponding imaging result. A health condition of the body-part is evaluated according to the imaging result. However, the proposed method may find application in any kind of diagnostic applications in the broadest meaning of the term (for example, in-vivo/ex-vivo, aimed at discovering new lesions, monitoring known lesions, assessing resected tissue for clinical decision making, and so on) and for analyzing any kind of body-part of any patient (see above).

An embodiment provides a therapeutic method comprising the following steps. A body-part of the patient is imaged according to the above-mentioned method so as to output the corresponding imaging result. The body-part is treated according to the imaging result. However, the proposed method may find application in any kind of therapeutic method in the broadest meaning of the term (for example, aimed at curing a pathological condition, at avoiding its progress, at preventing the occurrence of a pathological condition, or simply at ameliorating a comfort of the patient) and for acting on any kind of body-part of any patient (see above).

An embodiment provides a surgical method comprising the following steps. A body-part of the patient is imaged according to the above-mentioned method so as to output the corresponding imaging result. The body-part is operated according to the imaging result. However, the proposed method may find application in any kind of surgical method in the broadest meaning of the term (for example, for curative purposes, for prevention purposes, for aesthetic purposes, and so on) and for acting on any kind of body-part of any patient (see above).

In an embodiment, the diagnostic method, the therapeutic method and/or the surgical method comprise administering the luminescence agent to the patient. However, the luminescence agent may be administered in any way (see above), or this step may be omitted at all (in case the luminescence agent in intrinsic).

The invention claimed is:

1. A method for imaging an object containing a luminescence substance, wherein the method comprises:
   initializing, by a computing device, a combined image comprising a plurality of image values representative of corresponding locations of the object according to a starting imaging of the object or to default values,
   repeating, by the computing device, a refining loop comprising:
      segmenting, by the computing device, the combined image into a plurality of segments representative of corresponding regions of the object according to a segmenting criterion based on the image values of the combined image,
      determining, by the computing device, a plurality of spatial patterns according to the segmentation of the combined image,
      applying, by an illumination device a plurality of partial illuminations corresponding to the spatial patterns to the object in succession,
      acquiring, by an acquisition device, corresponding component images in response to the partial illuminations in succession, each of the component images comprising corresponding image values representative of a luminescence light being emitted by the luminescence substance from the locations of the object, and
      combining, by the computing device, the component images into a new version of the combined image
   until an exit condition of the refining loop is satisfied, and
   outputting, by an output device, an imaging result based on a last version of the combined image at an exit of the refining loop.

2. The method according to claim 1, wherein the luminescence substance is a fluorescence substance.

3. The method according to claim 1, wherein the method comprises:
   applying, by the illumination device, a starting illumination to the object,
   acquiring by the acquisition device, a starting image in response to the starting illumination, the starting image comprising corresponding image values representative of the luminescence light being emitted by the luminescence substance from the locations of the object, and
   initializing, by the computing device the combined image according to the starting image.

4. The method according to claim 3, wherein the method comprises:
   applying, by the illumination device, the starting illumination to the object providing a full illumination thereof.

5. The method according to claim 1, wherein the method comprises:
   segmenting, by the computing device, the combined image into at least one detection segment of the segments representative of a detection one of the regions wherein the luminescence agent is detected and at least one non-detection segment of the segments representative of a non-detection one of the regions wherein the luminescence agent is not detected.

6. The method according to claim 5, wherein the method comprises:
   determining, by the computing device, a main one of the spatial patterns for providing a full illumination of said at least one detection region and a non-illumination of said at least one non-detection region, and
   determining, by the computing device, a secondary one of the spatial patterns for providing a non-illumination of said at least one detection region and a full illumination of said at least one non-detection region.

7. The method according to claim 6, wherein the method comprises:
   combining, by the computing device, the component images into the combined image by cumulating the corresponding image values of the component images into each image value of the combined image.

8. The method according to claim 7, wherein the method comprises:
   combining by the computing device, the component images into the combined image by setting each image value of the combined image according to a sum of the corresponding image values of the component images.

9. The method according to claim 5, wherein the method comprises:
   determining, by the computing device, a main one of the spatial patterns for providing a prevalent illumination distributed throughout said at least one detection region, and
   determining, by the computing device, a secondary one of the spatial patterns for providing a prevalent illumination distributed throughout said at least one non-detection region.

10. The method according to claim 9, wherein the method comprises:
    determining, by the computing device, the main spatial pattern for providing a prevalent non-illumination distributed throughout said at least one non-detection region, and
    determining, by the computing device, the secondary spatial pattern for providing a prevalent non-illumination distributed throughout said at least one detection region.

11. The method, according to claim 10, wherein the prevalent illumination provides an illumination distributed randomly with a high spatial frequency and the prevalent non-illumination provides an illumination distributed randomly with a low spatial frequency lower than the high spatial frequency.

12. The method according to claim 11, wherein the method comprises:
    initializing, by the computing device, at least one of the spatial patterns for providing a full illumination of each one of the regions to be provided the prevalent illumination and for providing a non-illumination of each one of the regions to be provided the prevalent non-illumination, and adding, by the computing device, a pseudo-random illumination noise to each of the spatial patterns being initialized.

13. The method according to claim 9, wherein the method comprises:

combining, by the computing device, the component images into the combined image by differentiating the corresponding image value of the component image resulting from the main spatial pattern and the corresponding image value of the component image resulting from the secondary spatial pattern into each image value of the combined image.

14. The method according to claim 13, wherein the method comprises:

combining, by the computing device, the component images into the combined image by setting each image value of the combined image according to a difference between the corresponding image value of the component image resulting from the main spatial pattern and the corresponding image value of the component image resulting from the secondary spatial pattern.

15. The method according to claim 9, wherein the method comprises:

applying, by the illumination device, a starting illumination to the object, acquiring, by the acquisition device, a starting image in response to the starting illumination, the starting image comprising corresponding image values representative of the luminescence light being emitted by the luminescence substance from the locations of the object, initializing, by the computing device, the combined image according to the starting image, and reversing, by the computing device, the last version of the combined image by setting each image value thereof according to a difference between the corresponding image value of the starting image and the corresponding image value of the last version of the combined image.

16. The method according to claim 1, wherein the spatial patterns of each iteration of the refining loop combine to provide a full illumination of the object.

17. The method according to claim 1, wherein the method comprises:

verifying, by the computing device, the exit condition according to the combined image.

18. The method according to claim 17, wherein the method comprises:

verifying, by the computing device, the exit condition according to a similarity of a current version of the combined image resulting from a current iteration of the refining loop different from a first iteration of the refining loop with respect to at least one previous version of the combined image resulting from a previous iteration of the refining loop.

19. The method according to claim 1, wherein the object is a body-part of a patient.

20. The method according to claim 19, wherein a luminescence agent has been pre-administered to the body-part before performing the method.

21. A computing device configured for executing a computer program causing the computing device to perform the method according to claim 1.

22. A system comprising means configured for performing the steps of the method according to claim 1.

23. A system comprising a circuitry configured for performing each of the steps of the method according to claim 1.

24. A diagnostic method comprising:

imaging a body-part of a patient according to the method of claim 1 to output the imaging result, and evaluating a health condition of the body-part according to the imaging result.

25. A therapeutic method comprising:

imaging a body-part of a patient according to the method of claim 1 to output the imaging result, and treating the body-part according to the imaging result.

26. A surgical method comprising:

imaging a body-part of a patient according to the method of claim 1 to output the imaging result, and operating the body-part according to the imaging result.

27. A method for imaging an object containing a luminescence substance, wherein the method comprises:

repeating, by the computing device, a refining loop comprising:

determining, by the computing device, a plurality of spatial patterns, the spatial patterns being pre-defined at a first iteration of the refining loop and being defined by applying a preset modification to a previous version thereof at each next iteration of the refining loop, applying, by an illumination device, a plurality of partial illuminations corresponding to the spatial patterns to the object in succession, acquiring, by an acquisition device, corresponding component images in response to the partial illuminations in succession, each of the component images comprising a plurality of image values representative of a luminescence light being emitted by the luminescence substance from corresponding locations of the object, and combining, by the computing device, the component images into a new version of a combined image comprising corresponding image values representative of the luminescence light being emitted by the luminescence substance from the locations of the object until an exit condition of the refining loop is satisfied, and outputting, by an output device, an imaging result based on a last version of the combined image at an exit of the refining loop.

28. A non-transitory computer program product comprising a non-transitory computer readable storage medium storing a computer program, the computer program being loadable into a working memory of a computing device thereby configuring the computing device to perform the method according to claim 27.

* * * * *